United States Patent
Noble et al.

(10) Patent No.: US 9,725,697 B2
(45) Date of Patent: Aug. 8, 2017

(54) CHONDROGENIC PROGENITOR CELLS, PROTOCOL FOR DERIVATION OF CELLS AND USES THEREOF

(71) Applicant: The University Court of The University of Edinburgh, Edinburgh (GB)

(72) Inventors: Brendon Stewart Noble, Ipswich (GB); David Matthew Pier, Edinburgh (GB)

(73) Assignee: The University Court of The University of Edinburgh, Edinburgh (GB)

( * ) Notice: Subject to any disclaimer, the term of this patent is extended or adjusted under 35 U.S.C. 154(b) by 0 days.

(21) Appl. No.: 14/708,606

(22) Filed: May 11, 2015

(65) Prior Publication Data
US 2015/0240208 A1   Aug. 27, 2015

Related U.S. Application Data

(63) Continuation of application No. 13/082,727, filed on Apr. 8, 2011, now Pat. No. 9,029,145.

(60) Provisional application No. 61/321,982, filed on Apr. 8, 2010.

(51) Int. Cl.
| | |
|---|---|
| *C12N 5/00* | (2006.01) |
| *C12N 5/02* | (2006.01) |
| *C12N 5/077* | (2010.01) |
| *C12N 5/0775* | (2010.01) |
| *A61K 35/32* | (2015.01) |
| *G01N 33/50* | (2006.01) |

(52) U.S. Cl.
CPC ............ *C12N 5/0655* (2013.01); *A61K 35/32* (2013.01); *C12N 5/0662* (2013.01); *G01N 33/5044* (2013.01); *C12N 2500/25* (2013.01); *C12N 2500/84* (2013.01); *C12N 2500/90* (2013.01); *C12N 2501/15* (2013.01); *C12N 2501/39* (2013.01); *C12N 2506/02* (2013.01); *C12N 2506/03* (2013.01)

(58) Field of Classification Search
CPC .................................................. C12N 5/0655
See application file for complete search history.

(56) References Cited

U.S. PATENT DOCUMENTS

| | | |
|---|---|---|
| 5,843,780 A | 12/1998 | Thomson |
| 6,090,622 A | 7/2000 | Gearhart et al. |
| 6,150,163 A | 11/2000 | McPherson et al. |

FOREIGN PATENT DOCUMENTS

| | | |
|---|---|---|
| EP | 1792977 A1 | 6/2007 |
| WO | 96/18728 A1 | 6/1996 |
| WO | 98/55594 A2 | 12/1998 |
| WO | 00/27996 A1 | 5/2000 |
| WO | 03/004605 A2 | 1/2003 |
| WO | 03/050250 A2 | 6/2003 |
| WO | 2006/092633 A1 | 9/2006 |
| WO | 2007/052935 A1 | 5/2007 |
| WO | 2007/122233 A1 | 11/2007 |

OTHER PUBLICATIONS

Tong, Zhi-Chao et al., "Study of inducing bone marrow-derived mesenchymal stem cells into chondrocytes in vitro", China J. Orthop. & Trauma 21(5), 2008, 362-364.
Eisenberg, L.M. et al., "Stem cell plasticity, cell fusion, and transdifferentiation," Birth Defects Res C Embryo Today. 69(3), 2003, 209-18.
Khan, N.S. et al., "Potential of Human Embryonic Stem Cell-Derived Chondrogenic Cells to Repair an Anticular Defect," Osteoarthr. Cartil. vol. 17 abstract 488, 2009, S262.
Khan, N.S. et al., "Regenerative Properties of Human Embryonic Stem Cell-Derived Chondrogenic Cells in an Articular Defect," Euro. Cell. Mater. vol. 18, 2009, 48.
Koelling, S. et al., "Migratory chondrogenic progenitor cells from repair tissue during the later stages of human osteoarthritis," Cell Stem Cell. 3;4(4), 2009, 324-35.
Marlovits, S. et al., "Cartilage repair: generations of autologous chondrocyte transplantation," Eur J Radiol. Jan;57(1), 2006, 24-31.
Takahashi, K et al., "Induction of pluripotent stem cells from mouse embryonic and adult fibroblast cultures by defined factors," Cell. 25; 126(4), 2006, 663-76.
Yang, Z. et al., "Stage-dependent effect of TGF-beta1 on chondrogenic differentiation of human embryonic stem cells," Stem Cells Dev. 18(6), 2009, 929-40.
Benya, P. et al., "Dedifferentiated chondrocytes reexpress the differentiated collagen phenotype when cultured in agarose gels," Cell 30, 1982, 215-24.
Brittberg, M. "Autologous Chondrocyte Transplantation," Clin. Orthop. Related Res. 367Suppl., 1999, S147-55.
Ginis, I. et al., "Differences between human and mouse embryonic stem cells," Dev. Biol. 269, 2004, 360-80.
Hegert, C. et al., "Differentiation Plasticity of Chondrocytes Derived from Mouse Embryonic Stem Cells," J. Cell Sci. 115, 2002, 4617-28.
Jakob, M. et al., "Specific Growth Factors During the Expansion and Redifferentiation of Adult Human Articular Chondrocytes Enhance Chondrogenesis and Cartilaginous Tissue Formation in Vitro," J. Cell. Biochem. 81, 2001, 368-77.
Jorgensen, C. et al., "Stem Cells for Repair of Cartilage and Bone: The Next Challenge in Osteoarthritis and Rheumatoid Arthritis," Ann. Rheum. Dis. 60, 2001, 305-9.

(Continued)

*Primary Examiner* — Valarie Bertoglio
(74) *Attorney, Agent, or Firm* — Krista P. Kauppinen

(57) ABSTRACT

The present invention provides an isolated population of chondrocyte precursor cells wherein 1% or less of the cells express Oct4, Nanog and/or TRA-1-60, 7% or less of the cells express no collagen II, collagen X, CD105 or Stro-1 and 85% or more of the cells express CBFA1, methods for preparing such cells and uses of chondrocyte cells derived from said precursor cells.

5 Claims, 5 Drawing Sheets

(56) References Cited

OTHER PUBLICATIONS

Figure 1:
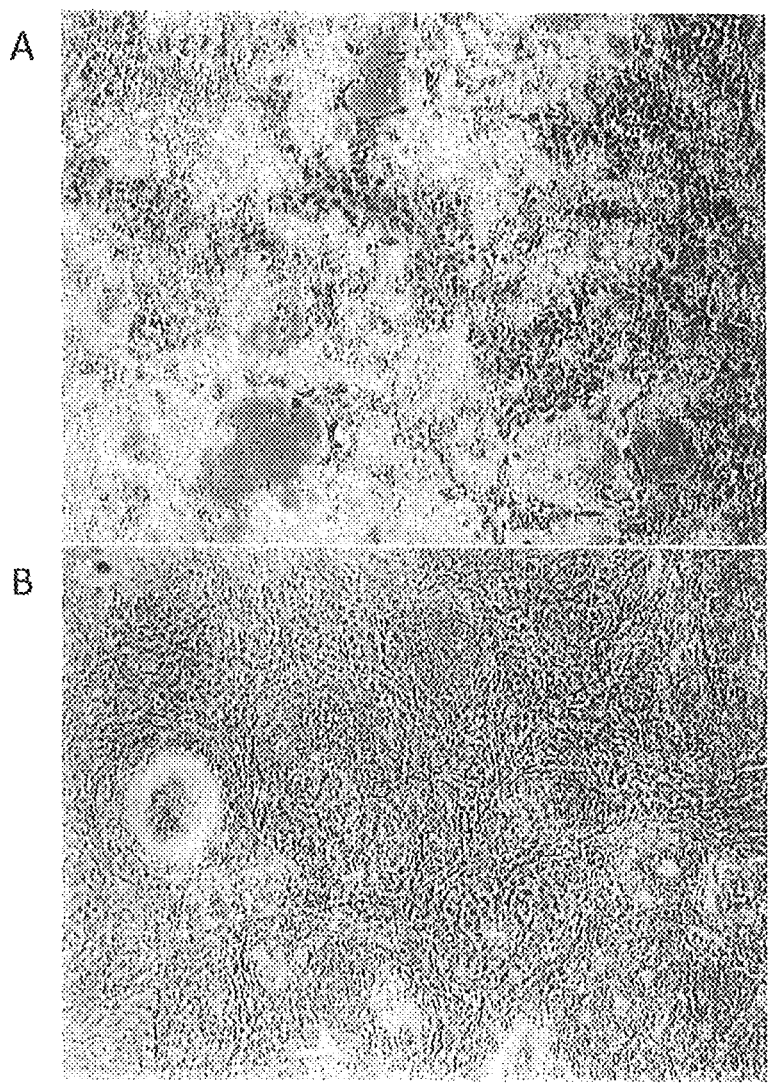

Kramer, J. et al., "Embryonic stem cell-derived chondrogenic differentiation in vitro: Activation by BMP-2 and BMP-4," Mech. Dev. 92(2), 2000, 193-205.
Shamblott, M. et al., "Derivation of pluripotent stem cells from cultured human primordial germ cells," Proc. Natl. Acad. Sci. USA 95, 1998, 13726-31.
Sottile, V. et al., "In vitro osteogenic differentiation of human ES cells," Cloning Stem Cells 5(2), 2003, 149-55.
Takeda, S. et al., "Continuous expression of Cbfa1 in nonhypertrophic chondrocytes uncovers its ability to induce hypertrophic chondrocyte differentiation and partially rescues Cbfa1-deficient mice," Genes Dev. 15(4), 2001, 467-81.
Thomson, J. et al., "Embryonic stem cell lines derived from human blastocysts," Science 282, 1998, 1145-7.
Thomson, J. et al., "Isolation of a primate embryonic stem cell line," Proc. Natl. Acad. Sci. USA 92, 1995, 7844-8.
Toh, et al., "Differentiation and enrichment of expandable chondrogenic cells from human embryonic stem cells in vitro," J. Cell. Mol. Med. 13(9B), 2009, 3570-90.

CHONDROGENIC PROGENITOR CELLS, PROTOCOL FOR DERIVATION OF CELLS AND USES THEREOF

REFERENCE TO RELATED APPLICATIONS

This application is a continuation of and claims priority to U.S. patent application Ser. No. 13/082,727 (now U.S. Pat No. 9,029,145) filed on Apr. 8, 2011, which claims priority to U.S. Provisional Application No. 61/321,982, filed on Apr. 8, 2010. The entire contents of both priority documents are hereby incorporated by reference.

TECHNICAL FIELD

The present invention relates generally to the fields of cell biology, embryonic stem cells, and cell differentiation. The invention discloses chondrogenic progenitor cells and a method for the preparation of such cells and fully differentiated chondrocytes, including uses of the cells.

BACKGROUND

Chondrocytes are specialised cells found in cartilage. Chondrocytes in cartilage produce a large amount of extracellular matrix which is composed of collagen fibers, ground substance, which is rich in proteoglycan, and elastin fibers. The cartilage tissue performs a structural and mechanical function in skeletal joints and any disease or injury is consequently debilitating for patients.

Cartilage degradation is a hallmark of two disease groups: osteoarthritis, a degenerative condition, and rheumatoid arthritis, which is primarily caused by inflammation. The degradation leads to joint pain and mobility impairment to a degree that can be disabling.

Considerable progress has been made in the development of anti-inflammatory agents effective for inhibiting the progress of such diseases. However, where degradation or injury has already taken place, new therapies are needed to assist in the regenerating of joint cartilage.

In the field of regenerative medicine, efforts have been directed at developing cell populations capable of repairing cartilage. Established lines of articular chondrocytes have been described in WO 96/18728 and methods for chondrocyte growth and differentiation have been reported in WO 98/55594. WO 00/27996 reports serum-free medium for chondrocyte like cells, comprising minimum essential medium, growth factors, lipids and amino acids. U.S. Pat. No. 6,150,163 outlines chondrocyte media formulations and culture procedures, in which de-differentiated human articular chondrocytes are grown in a medium containing TGFβ and either insulin or insulin-like growth factor. It has also been reported that primary chondrocytes cultured in vitro will de-differentiate if not treated with the appropriate factors (Benya et al. Cell 1982 30:215). The cells that are produced are fibroblastic in appearance and may be MSC-like.

Jorgensen et al. (Ann. Rheum. Dis. 60:305, 2001) reviews recent progress in stem cells for repair of cartilage and bone in arthritis. Jakob et al. (J. Cell. Biochem. 26:81, 2001) studied specific growth factors involved in expansion and redifferentiation of adult human articular chondrocytes that enhance chondrogenesis and cartilage formation. M. Brittberg (Clin. Orthop. 367 Suppl:S147, 1999) reviews current chondrocyte transplantation procedures in which pure chondrocytes or other mesenchymal cells are harvested autologously or as allografts from a healthy tissue source, expanded in vitro, and then implanted into the defect at high density.

Despite the initial success of the clinical methods reported to date, it is clear that current sources of chondrocytes are inadequate to treat most of the instances of cartilage degeneration that present themselves at the clinic. In addition, problems concerning the use of immunosuppressive drugs have complicated the success of developing new transplantation protocols.

Regenerative medicine is also benefiting from recent advances relating to the isolation, culture, and use of various types of progenitor cells. Embryonic stem cells have two very special properties: First, unlike other typical mammalian cell types, they can be propagated in culture almost indefinitely while maintaining their pluripotency, providing a virtually unlimited supply. Second, they can be used to generate a variety of tissue types of interest as a source of replacement cells and tissues for use in tissue therapy, or for use in the screening of pharmaceutical agents. Consequently, stem cells are seen as possible sources of chondrocytes.

Kramer et al. (Mech. Dev. 92:193, 2000) reported that mouse embryonic stem cells can be modulated with bone morphogenic proteins (BMP-2 and BMP-4) to produce cells that stained with Alcian blue, a feature of chondrocytes, and expressing the transcription factor scleraxis. However, the mouse model of embryonic stem cell development does not necessarily yield strategies for differentiation that are applicable to other species (see, e.g. Ginis et al. (2004) Dev. Biol 269:360).

Thomson et al. (U.S. Pat. No. 5,843,780; Proc. Natl. Acad. Sci. USA 92:7844, 1995) were the first to successfully isolate and propagate pluripotent stem cells from primates. They subsequently established human embryonic stem (hES) cell lines from human blastocysts (Science 282:114, 1998). Gearhart and co-workers established human embryonic germ (hEG) cell lines from fetal gonadal tissue (Shamblott et al., Proc. Natl. Acad. Sci. USA 95:13726, 1998; and U.S. Pat. No. 6,090,622). Both hES and hEG cells have the long-sought characteristics of pluripotent stem cells: they can be cultured extensively without differentiating, they have a normal karyotype, and they are capable of producing a number of important cell types including cell types from all three primary germ layers.

Mesenchymal progenitors can be generated from hES cells according to the method described in WO 03/004605. The hES-derived mesenchymal cells can then be further differentiated into osteoblast lineage cells in a medium containing an osteogenic factor, such as bone morphogenic protein (particularly BMP-4), a ligand for a human TGF-β receptor, or a ligand for a human vitamin D receptor (WO 03/004605; Sotile et al., Cloning Stem Cells 2003; 5(2):149-55). Chondrocytes or their progenitors can be generated by culturing hES cells in microaggregates with effective combinations of differentiation factors listed in WO 03/050250.

Hegert et al. (J. Cell Sci. 115:4617, 2002) reported the differentiation plasticity of chondrocytes derived from embryoid bodies composed of mouse embryonic stem cells. Toh et al. describes differentiation and enrichment of expandable chondrogenic cells from human embryonic stem cells in vitro (J. Cell. Mol. Med., 2009—early online publication citation reference 10.1111/j.1582-4934.2009.00762.x).

There remains a need for efficient, scaleable methods capable of producing sufficient quantities of chondrocyte lineage cells, including both chondrocyte progenitors as well as mature chondrocytes for therapeutic and research applications. It would also be useful if a stable chondrocyte precursor could be isolated that could be maintained in culture under scaleable conditions and which could readily be differentiated into mature chondrocytes or cells expressing proteins, such as collagen II, aggrecan and glycosaminoglycans.

However, even with the preparation of chondrocytes derived from undifferentiated progenitor cell populations, such as hES cells, there remains the need to use immunosuppressive drugs in transplantation therapies using chondrocyte cell populations which is unfavourable for the long term success of transplants in patients.

Accordingly, it is necessary to develop a new approach to differentiate primate pluripotent cells into fully functional chondrocytes which avoid the need to use immunosuppressant drugs in transplantation as well as the chondrocyte precursor cells types which could readily give rise to such chondrocytes. It is also necessary to develop a new approach to therapeutically using chondrocytes, such as chondrocytes differentiated in vitro from primate pluripotent stem cells, without the use of immunosuppressive and/or anti-inflammatory agents. It is further necessary to develop a new approach to treating subjects with chondrocytes, such as chondrocytes differentiated in vitro from primate pluripotent stem cells, without the use of immunosuppressive and/or anti-inflammatory agents.

SUMMARY OF THE INVENTION

The present invention provides a novel population of chondrocyte progenitor or precursor cells which are characterised by the expression of certain protein markers as defined herein. The cells may also be characterised by the loss of transdifferentiation potential The population of chondrocyte precursors or progenitors can be obtained by differentiating pPS cells by a method of the present invention, and is capable of forming progeny having the characteristics of mature chondrocytes. The chondrocyte progenitors are no longer pluripotent, but are committed to the chondrocyte development pathway The invention also provides a system as defined herein for the preparation of chondrocytes and chondrocyte progenitor or chondrocyte precursor cells. The isolated or in vitro population of chondrocyte progenitor or chondrocyte precursor cells is prepared by differentiating a population of primate pluripotent stem (pPS) cells in chondrogenic media until the cells are greater than 75% confluent after which the cells are washed and resuspended in a defined minimal growth media and cultured for a further period until the cells are differentiated into a population of cells which are characterised by the loss of transdifferentiation potential, e.g. the cells cannot be subsequently cultured in osteogenic media to form osteoblasts. The cells of this culture are also characterised by a fibroblast morphology, the absence of expression of ES pluripotency markers or mesenchymal stem cell (MSC) markers, and the absence of expression of chondrogenesis markers. The cells of this culture are also characterised by the presence of expression of nuclear markers for hypertrophic chondrocytes and osteogenesis. This feature therefore distinguishes the cells from primary (non-hypertrophic) chondrocytes.

Suitable assays to detect these markers are described herein. Pluripotency markers include Oct4, Nanog and/or TRA-1-60. Markers of chondrogenesis include collagen II. Nuclear markers for hypertrophic chondrocytes and osteogenesis include CBFA1/RunX2.

The loss of transdifferentiation potential, e.g., that the cells cannot be subsequently cultured in osteogenic media to form osteoblasts, can be shown by the absence of mineralisation in the chondrocyte precursor cells upon further culture in osteogenic media.

Characterisation by expression markers of chondrocyte progenitor or chondrocyte precursor cells prepared according to a method of the invention is shown in Table 1, with an absence of expression ("negative") being indicated thus "−" and the presence of expression ("positive") being indicated thus "+":

TABLE 1

| Marker | Expression status (−/+) | Characteristic |
|---|---|---|
| Nanog | − | pluripotency |
| Oct4 | − | pluripotency |
| Tra-1-60 | − | pluripotency |
| Collagen II | low | chondrogenesis |
| CBFA1/RunX2 | + | hypertrophic chondrocytes/osteogenesis |
| Collagen X | − | hypertrophic chondrocytes |
| Osteocalcin | − | osteogenesis |
| CD105 | − | chondrocytes |
| Stro-1 | − | mesenchymal stem cells |

Less than about 7% of the cells in a population express no Collagen II, whereas the remainder 93% of the population express a low level of the marker. Expression of this marker is therefore less than the level of expression seen in a population of fully differentiated chondrocytes.

The chondrocyte progenitor or chondrocyte precursor cells are distinguished from previously known chondrocyte cells or precursor cells in view of the above properties. The cells may be referred to as dedifferentiated committed chondrocyte progenitor cells (DCCPC) or Induced chondrocyte precursor cells (ICPC) by virtue of the means used to prepare the cells. In view of the ability of the cells to be subsequently differentiated into chondrocytes, the cells may also be described as "Forward-Back Chondrocytes" or FBCs. Any of these terms may be used interchangeably.

The DCCPC can be further cultured in chondrogenic media after washing. Subsequent culture yields a population of cells that can be characterised as chondrocytes using the markers collagen II and collagen X. The chondrocytes produced express high levels of collagen II but little or no collagen X.

The present invention also provides populations of chondrocytes differentiated from DCCPC prepared according to the present invention for use in transplantation. Surprisingly, the fully differentiated chondrocyte cell populations may be administered to a subject without immuno-suppressive compounds such as FK-506, cyclosporin or the like. Moreover, anti-inflammatory agents such as prednisone and the like are not required either. This embodiment of the invention extends to a method of treating a degenerative cartilage disease or cartilage injury comprising transplanting a population of chondrocyte cells prepared DCCPC of the present invention into a subject in need thereof.

The invention also provides an isolated or in vitro cell population containing chondrocytes, obtained by differentiating the DCCPC described herein. Chondrocyte lineage cells can be identified by the ability to synthesize for example Type II collagen or aggrecan from an endogenous gene. Preferably, the population contains a minimal proportion of cells that synthesize elastic cartilage, fibrocartilage, hypertrophic cartilage or bone.

The proportion of undifferentiated pluripotent cells in the population is preferably minimized, and any residual undifferentiated cells are not the cells responsible for forming the chondrocytes upon further proliferation.

Another embodiment of the invention is a method for producing cartilage by incubating a cell population of this invention under conditions where connective tissue proteins are produced. Another embodiment of the invention is a method of screening a compound for its ability to modulate chondrocyte growth, differentiation, or synthesis of cartilage components, by combining the compound with a cell population of the invention and determining its effect.

Another embodiment of the invention is a method of differentiating pPS cells in vitro into chondrocytes comprising culturing the pPS in a media suitable for differentiating the pPS cells into chondrocyte precursor cells (and optionally isolating the chondrocyte precursor cells) and then changing the culture conditions such that the chondrocyte precursors de-differentiate into cells with a fibroblast-like morphology and nuclear CBFA-1 expression, followed by subsequent re-differentiation of the cells into fully differentiated chondrocytes.

Optionally, replication capacity of the stem cells, such as primate pluripotent stem cells or human embryonic stem cells, can be improved by increasing telomerase activity.

Another embodiment of the invention is a pharmaceutical composition for producing, repairing, or maintaining cartilage in vivo, containing a cell population of this invention or a fully differentiated chondrocyte cell population derived therefrom—and the use of such medicaments for reconstructing cartilage in a subject, including articular cartilage, for example, in cosmetic surgery or the treatment of joint trauma, arthritis, or osteoarthritis.

These and other embodiments of the invention are further described as follows.

DRAWINGS

FIG. 1 shows morphology changes through the DCCPC protocol. After the initial chondrogenic differentiation for 14 days H7 cells condense into dense three dimensional colonies. A large amount of cell death is observed and is seen here as phase bright clusters on top of the live adherent cells (A). After 5 days in the de-differentiation media cells have migrated out from the three dimensional colonies into the free space around them to form a monolayer of fibroblast like cells (B).

Figure 2:
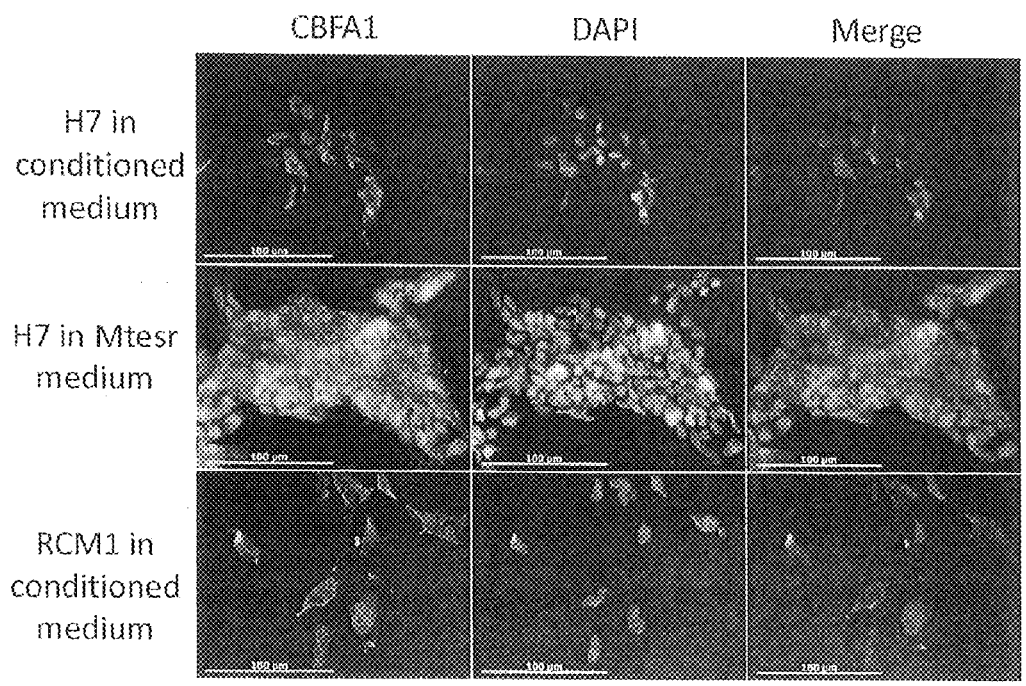

FIG. 2 shows nuclear CBFA-1 protein expression in DCCPC by CBFA-1/RunX2 staining on DCCPC. H7 cells cultured in mTeSR™ or Conditioned Medium (CM) before entering the DCCPC protocol were stained with an anti-CBFA-1 antibody. The hESC line RCM1 was also stained with the same antibody. In all cases the CBFA-1 antibody co-localises with the DNA binding dye DAPI.

Figure 3:
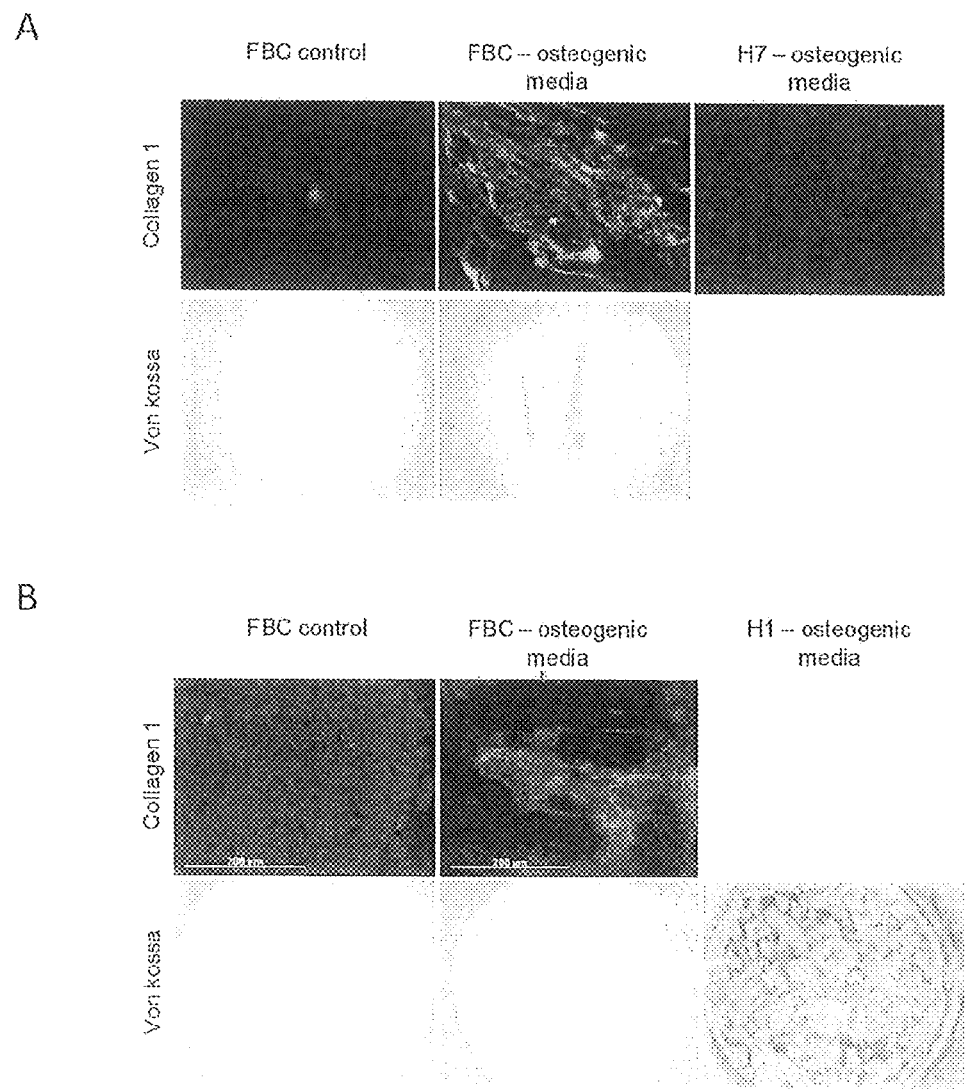

FIG. 3 shows presence of collagen type I and mineralisation in DCCPC differentiated with osteogenic media. DCCPC fail to mineralise matrix after osteogenic differentiation. DCCPC generated from H7 (A) and H1 (B) cell lines show an increase in extracellular collagen type I protein production after culture in osteogenic media. The Von Kossa staining protocol will give a dark brown/black stain when calcium deposits are present. The absence of staining in both cell lines indicates the absence of calcium and therefore the absence of matrix mineralisation.

Figure 4:
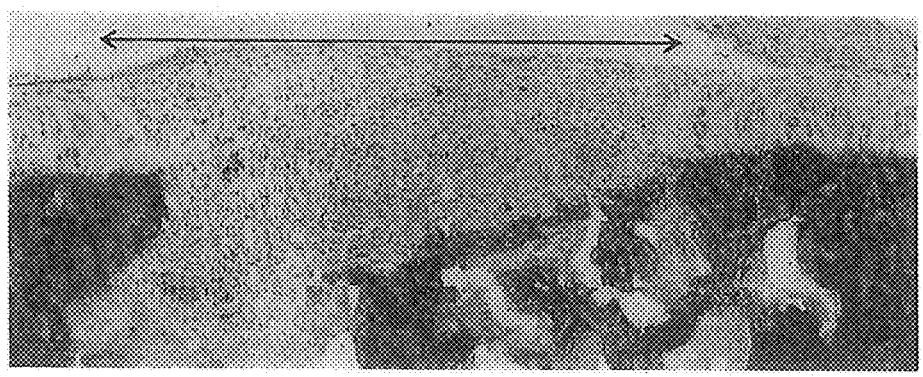

FIG. 4 shows promotion of in vivo cartilage repair by DCCPC after 21 days in a WT rat using re-differentiated DCCPC. DCCPC generated from H7 line previously cultured in CM were cultured in a construct format and implanted into WT rats. One construct was placed into a 1 mm defect in the trochlea groove of the rat hind limb. After 21 days the limb was cryosectioned and stained with H&E. The arrow indicates the extent of the regenerated material.

Figure 5:
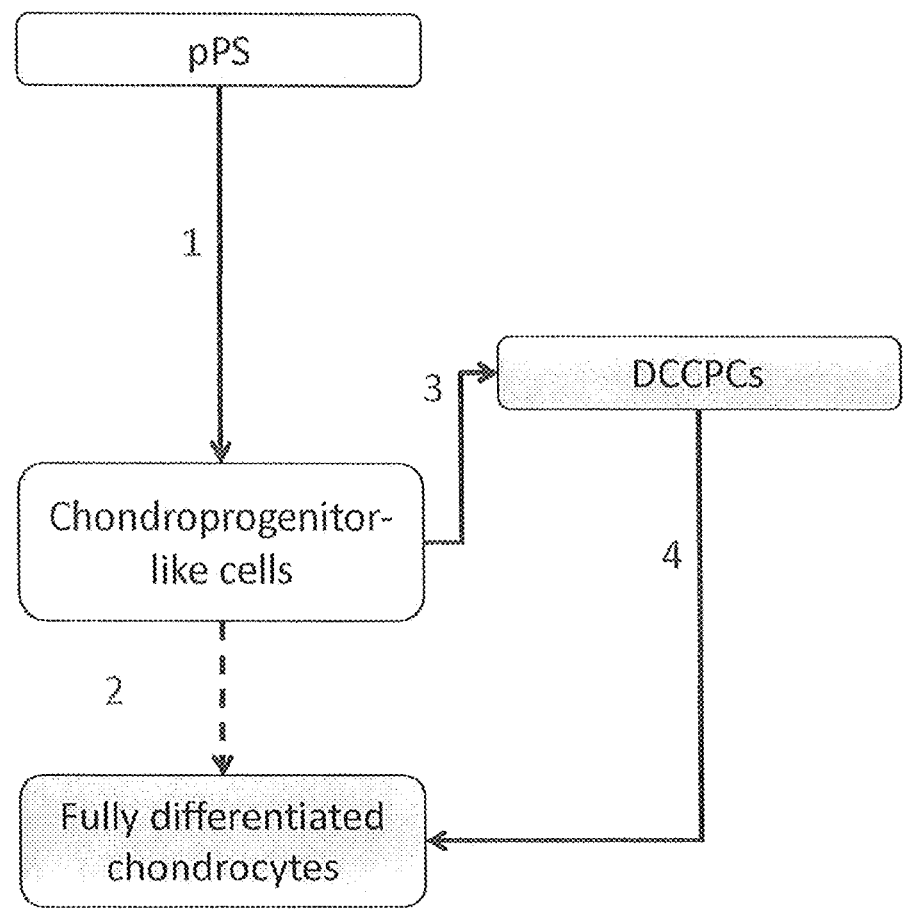

FIG. 5 shows a schematic representation of DCCPC protocol. Using chondrogenic media pPS are differentiated towards chondroprogenitor-like cells (1). This process is characterised by high cell death, loss of pluripotency and multipotency markers and the initiation of collagen type II production. Further application of chondrogenic media produces fully differentiated chondrocytes but is not part of the DCCPC protocol (2), instead the chondrocyte precursor cells are incubated with de-differentiation media until the cells show a fibroblast-like morphology and nuclear CBFA-1 expression. The absence of pluripotency and multipotency markers is maintained (3). The DCCPC can then be re-differentiated to fully differentiated chondrocytes using chondrogenic media (4).

DETAILED DESCRIPTION

This invention provides a means to prepare populations of DCCPC with important and useful properties. They can be grown and maintained in bulk and then readily differentiated into cells that express collagen II, such as mature chondrocytes. The differentiated chondrocytes prepared from such cells can be used in applications such as transplantation therapy and screening methods as described herein.

The disclosure that follows provides a full description of how to make the chondrocyte precursor cells of this invention, as well as chondrocytes derived therefrom. It provides extensive illustrations of how these cells can be used in research and pharmaceutical development. The disclosure also provides pharmaceutical compositions, devices, and treatment methods for the use of DCCPC for regeneration and remodelling of cartilage to restore joint mobility and for cosmetic purposes.

Definitions

For purposes of this disclosure, unless otherwise specified, the term "chondrocyte" refers to mature cells capable of modelling cartilage by the synthesis of Type II collagen and aggrecan. The term "dedifferentiated committed chondrocyte progenitor cells (DCCPC)" is used to refer to specialised progenitor cells prepared by a method of the present invention that can be differentiated to form mature chondrocytes and which are characterized by the marker expression profile described infra. Cells of a chondrocyte morphology have a rounded-up cell body and in a chondrogenic culture the cells cluster into dense colonies.

In the context of cell ontogeny, the adjective "differentiated" is a relative term. A "differentiated cell" is a cell that has progressed further down the developmental pathway than the cell it is being compared with.

A "differentiation agent", as used in this disclosure, refers to one of a collection of compounds that are used in culture systems of this invention to produce differentiated cells of the chondrocyte lineage (including precursor cells, such as DCCPC and terminally differentiated cells such as mature chondrocytes). No limitation is intended as to the mode of action of the compound. For example, the agent may assist the differentiation process by inducing or assisting a change in phenotype, promoting growth of cells with a particular phenotype or retarding the growth of others. It may also act as an inhibitor to other factors that may be in the medium or synthesized by the cell population that would otherwise direct differentiation down the pathway to an unwanted cell type.

Prototype "primate Pluripotent Stem cells" (pPS cells) are pluripotent cells capable under the right conditions of producing progeny of several different cell types. pPS cells are capable of producing progeny that are derivatives of each of the three germ layers: endoderm, mesoderm, and ectoderm, according to a standard art-accepted test, such as the ability to form a teratoma in a suitable host, or the ability to differentiate into cells having markers for tissue types of all three germ layers in culture.

Included in the definition of pPS cells are embryonic cells of various types, exemplified by hES cells, defined below; embryonic stem cells from other primates, such as Rhesus or marmoset stem cells (Thomson et al., Proc. Natl. Acad. Sci. USA 92:7844, 1995; Developmental Biology 38:133, 1998); and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. It is beneficial to use pPS cells that are karyotypically normal and not derived from a malignant source.

pPS cells include cells and established cell lines. The cells may be derived from pre-embryonic, embryonic, or fetal tissue at any time after fertilization. as Also included in the term are induced pluripotent stem (iPS) cells, which have the characteristic described above (see, e.g., Takahashi et al. (2007) Cell 131:1).

Primate pluripotent stem cells typically express the stage-specific embryonic antigens (SSEA) 3 and 4, and markers detectable using antibodies designated TRA-1-60 and TRA-1-81. Undifferentiated pPS cells also typically express the transcription factor Oct 3/4, Cripto, gastrin-releasing peptide (GRP) receptor, podocalyxin-like protein (PODXL), nanog and telomerase reverse transcriptase, e.g., hTERT (US 2003/0224411 A1), as detected by RT PCR.

Prototype "human Embryonic Stem cells" (hES cells) are described by Thomson et al. (Science 282:1145, 1998; U.S. Pat. No. 6,200,806). The scope of the term covers pluripotent stem cells that are derived from a pre-implantation blastocyst, such as an in vitro fertilized egg, before substantial differentiation of the cells into the three germ layers. Those skilled in the art will appreciate that except where explicitly required otherwise, the term includes primary tissue and established lines that bear phenotypic characteristics of hES cells, and derivatives of such lines that still have the capacity of producing progeny of each of the three germ layers.

pPS cell cultures, such as hES cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells on an ongoing basis, and may contain at least 40%, 60%, or 80% in order of increasing preference (in terms percentage of cells with the same genotype that are undifferentiated).

As discussed above, other sources of pluripotent cells include induced pluripotent stem (iPS) cells. The iPS cells can be prepared by the technique of Yamanaka et al. using retroviral infection of fibroblasts with genes Oct-3/4, SOX2, c-Myc, and Klf4. Selection of iPS cells using the marker Nanog appears to be advantageous (Takahashi, K. & Yamanaka, S., Cell, 126:663, 2006; Yamanaka S, et al. Nature 448:313, 2007; Wernig M, et al. Nature 448:318, 2007; Maherali N, et al. Cell Stem Cell 1:55, 2007). More recently, Thomson et al. used a slightly altered mix of genes OCT4, SOX2, NANOG, and a different gene LIN28 using a lentiviral system (Science, 318:1917, 2007) and also successfully with non-integrating episomal vectors (Science, 324:797, 2009).

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

A "nutrient medium" is a medium for culturing cells containing nutrients that promote proliferation. The nutrient medium typically contains isotonic saline, buffer, a protein source (in the form of one or more added proteins or amino acids), and potentially other exogenously added nutrients and growth factors.

A "chondrogenic medium" is comprised of essential minerals, amino acids, vitamins and substrates for the culture of cells as well as factors necessary for differentiating cells into chondrocytes. A typical chondrogenic medium may be comprised of a defined minimal growth medium supplemented by at least one hormone, growth factor, non-essential amino acid, and/or co-factor.

A "conditioned medium" is prepared by culturing a first population of cells in a medium, and then harvesting the medium. The conditioned medium (along with anything secreted into the medium by the cells) may then be used to support the growth of a second population of cells. Where a particular ingredient or factor is described as having been added to the medium, what is meant is that the factor (or a cell or particle engineered to secrete the factor) has been mixed into the medium by deliberate manipulation.

A "defined minimal growth medium" is comprised of essential minerals, amino acids, vitamins and substrates for the culture of cells. A typical defined growth medium may comprise one or more inorganic salt, amino acid, vitamin, sugar, buffer, indicator dye or colourant.

A "fresh medium" is a medium that has not been purposely conditioned by culturing with a different cell type before being used with the cell type it is ultimately designed to support. Otherwise, no limitations are intended as to its manner of preparation, storage, or use. It is added fresh (by exchange or infusion) into the ultimate culture, where it may be consumed or otherwise processed by the cell types that are present.

An "osteogenic medium" is composed of essential minerals, amino acids, vitamins and substrates for the culture of cells as well as factors necessary for differentiating cells into osteocytes. A typical osteogenic medium may be composed of a defined growth medium supplemented with one or more serum protein, amino acid, non-essential amino acid, and/or co-factor.

"Feeder cells" or "feeders" are terms used to describe cells of one type that are co-cultured with cells of another type, to provide an environment in which the cells of the second type can grow. Certain types of pPS cells can be supported by primary mouse embryonic fibroblasts, immortalized mouse embryonic fibroblasts, or human fibroblast-like cells differentiated from hES cell. pPS cell populations are said to be "essentially free" of feeder cells if the cells have been grown through at least one round after splitting in which fresh feeder cells are not added to support the growth of pPS cells.

The term "embryoid bodies" is a term of art synonymous with "aggregate bodies", referring to aggregates of differentiated and undifferentiated cells that appear when pPS cells overgrow in monolayer cultures, or are maintained in suspension cultures. The starting material for forming an embryoid body is a culture of undifferentiated pluripotent stem cells. Embryoid bodies are a mixture of different cell types, typically from several germ layers, as well at least some pluripotent cells distinguishable by morphological criteria and cell markers detectable by immunocytochemistry. Typically the number of pluripotent stem cells in the embryoid body decreases over time as the number of differentiated cells increases. Differentiation occurring in the context of an embryoid body is essentially a random event, thus each embryoid body cultured under identical conditions will typically not be identical in terms of the cellular composition. The term is distinguished from a construct culture used in the generation of chondrocyte lineage cells in that the starting material for a construct culture is not a culture that is primarily comprised of undifferentiated pluripotent stem cells, but rather is comprised of cells that have begun to differentiate away from the pluripotent state typically down the chondrocyte lineage pathway. Thus the starting material of a construct is a more developmentally advanced cell. Moreover construct cultures typically comprise one or more factors that specifically direct the differentiation of the culture down a desired pathway such as the chondrocytic pathway.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

Treat, treatment, treating, as used herein means any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition; the prophylaxis of one or more symptoms associated with a disease or condition.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current Protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of *Culture of Animal Cells: A Manual of Basic Technique* (R. I. Freshney ed., Wiley & Sons); *General Techniques of Cell Culture* (M. A. Harrison & I. F. Rae, Cambridge Univ. Press), and *Embryonic Stem Cells: Methods and Protocols* (K. Turksen ed., Humana Press). Other references of interest include *Culture Is Our Business* (M. McLuhan, Ballantine Books, 1970); and *Understanding Media* (M. McLuhan, Signet, 1970). Tissue culture supplies and reagents are available from commercial vendors such as Gibco/BRL, Nalgene-Nunc International, Sigma Chemical Co., and ICN Biomedicals.

General aspects of the biology and pathology of cartilage, and the role of chondrocytes in the maintenance of joints can be found in the following reference textbooks: *Mechanobiology: Cartilage and Chondrocyte*, by J. F. Stoltz ed., IOS Press 2000; *Biological Regulations of the Chondrocytes*, by M. Adolphe ed., CRC Press 1992; *Bone and Cartilage Allografts*, by G. E. Friedlaender et al. eds., Amer. Acad. Orthopaedic 1991; *Joint Cartilage Degradation*, by J. F. Woessner & D. S. Howell eds., Marcel Dekker 1992; *Skeletal Tissue Mechanics*, $2^{nd}$ edition by R. B. Martin et al., Springer Verlag 1998; *Molecular and Developmental Biology of Cartilage*, B. De Crombrugghe et al. eds., Ann. N.Y. Acad. Sci. Vol. 785: 1996; and *Joint Structure and Function: A Comprehensive Analysis*, $3^{rd}$ edition by P. K. Levangie et al. eds, F A Davis, 2000.

Preparation of Chondrocytes and Chondrocyte Progenitor Cells

Methods of the present invention provide a system as defined herein for the preparation of chondrocytes and chondrocyte progenitor or precursor cells. Cultures of hES cells are grown adherently, without forming an embryoid body to more than three-quarters complete confluency under standard hES culture conditions.

The media is then changed for a chondrogenic differentiation media as described herein and cultured for an appropriate period, e.g., about 13 to 15 days, suitably 14 days, washed and placed into de-differentiation media and cultured adherently without forming a construct culture for a further period as appropriate e.g., 4 to 6 days, suitably 5 days, trypsinised and resuspended. At this point the cells are distinct from isolated primary chondrocytes in terms of morphology and properties. Further culture of the cells in chondrogenic media for a further period of 21 days enables chondrocytes to be produced. However, culture of the same chondrocyte precursors in osteogenic media (comprising Dexamethasone, beta glycerol phosphate, ascorbic acid, sodium pryuvate and L-glutamine. A suitable base media may include commercially available Knockout™ D-MEM (Invitrogen) which may be supplied with serum) does not lead to the derivation of functional osteoblasts.

Suitable types of chondrogenic media include a media comprising dexamethasone, insulin, transferrin, selenious acid, bovine serum albumin, and linoleic acid, L-proline, ascorbic acid, sodium pyruvate and a TGF-β (for example TGF-β3). A suitable base media may include commercially available media such as DMEM (Life Technologies). The de-differentiation media may be DMEM supplemented with serum.

Suitable markers of chondrocyte differentiation include Collagen II and aggrecan, and suitable markers of pluripotency include Oct4, Tra-1-60 and Nanog.

Sources of Stem Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using primary mouse fibroblast feeder cells, according to the techniques described by Thomson et al. (U.S. Pat. No. 6,200,806; Science 282:1145, 1998; Curr. Top. Dev. Biol. 38:133, 1998) and Reubinoff et al., Nature Biotech. 18:399, 2000. hES cell lines can also be derived on human feeders (U.S. Pat. No. 6,642,048), or in conditions entirely free of feeder cells (US 2002/0081724) or Klimanskaya et al., Lancet, 365(9471):1636-41 (2005)). Equivalent cell types to hES cells include their pluripotent derivatives, such as primitive ectoderm-like (EPL) cells, as outlined in WO 01/51610. Embryonic stem cells may be chosen from embryonic stem cell lines or may be obtained directly from primary embryonic tissue.

By no means does the practice of this invention require that a human blastocyst be disaggregated in order to produce the hES or embryonic stem cells for practice of this invention. hES cells can be obtained from established lines obtainable from public depositories (for example, the WiCell Research Institute, Madison Wis. USA, or the American Type Culture Collection, Manassas Va., USA).

A number of embryonic stem cell lines have been established including, but not limited to, H1, H7, H9, H13 and H14 (Thompson et al.); hESBGN-01, hESBGN-02, hES-BGN-03 (BresaGen, Inc., Athens, Ga.); HES-1, HES-2, HES-3, HES-4, HES-5, HES-6 (ES Cell International, Inc., Singapore); HSF-1, HSF-6 (University of California at San Francisco); I 3, I 4, I 6 (Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Established hES cell lines may be obtained from various sources including the UK Stem Cell Bank (National Institute for Biological Standards and Control, UK), the National Stem Cell Bank (University of Wisconsin-Madison, USA) or WiCell (Madison, Wis., USA).

Human Embryonic Germ (hEG) cells can be prepared from primordial germ cells as described in Shamblott et al., Proc. Natl. Acad. Sci. U.S.A. 95:13726, 1998 and U.S. Pat. No. 6,090,622. US 2003/0113910 reports pluripotent stem cells derived without the use of embryos or fetal tissue. It may also be possible to reprogram other progenitor cells into hES cells by using a factor that induces the pluripotent phenotype (Chambers et al., Cell 113:643, 2003; Mitsui et al., Cell 113:631, 2003). Under appropriate conditions, any cell with appropriate proliferative and differentiation capacities can be used for the derivation of differentiated tissues for use according to this invention.

The propagation and maintenance of pPS cells such that the cells remain pluripotent has been described. pPS cells may be propagated and maintained using either a feeder cell layer or feeder free conditions (see, e.g. U.S. Pat. No. 5,843,780; U.S. Pat. No. 6,090,622, 6,800,480, WO 01/51616; WO 03/020920; WO 06/017370; WO 07/002086; WO 09/099539; WO 09/099555 and Xu et al. (2001) Nature Biotechnology 19:971, Many suitable commercially available base media have been developed for culturing proliferative cell types and thus are suitable for culturing pPS cell such as hES cells. Exemplary are X—VIVO™ 10 expansion medium (Biowhittaker) and QBSF™-60 (Quality Biological Inc.). See also WO 98/30679 (Life Technologies Inc.) and U.S. Pat. No. 5,405,772 (Amgen). The X-VIVO™ 10 formulation contains pharmaceutical grade human albumin, recombinant human insulin and pasteurized human transferrin. Exogenous growth factors, artificial stimulators of cellular proliferation or undefined supplements are not included in the X-VIVO™ 10 medium. They are also devoid of any protein-kinase C stimulators. QBSF™-60 is a serum-free formulation that contains recombinant or pasteurized human proteins. Other potential alternatives are Ex-Cell VPRO™ medium made by JRH Biosciences, and HyQ CDM4™ made by Hyclone and mTESR™ from StemCell Technologies.

The base medium may be supplemented with additives that promote proliferation of the undifferentiated phenotype while inhibiting differentiation. Fibroblast growth factor at high concentration is especially effective to promote hES cell proliferation without differentiation. Exemplary are basic FGF (FGF-2), and FGF-4, but other members of the family can also be used. Equivalent forms are species homologs, artificial analogs, antibodies to the respective FGF receptor, and other receptor activating molecules. It has been determined from gene expression analysis that undifferentiated hES cells express receptors for acidic FGF (FGF-1). At a high concentration, FGF alone is sufficient to promote growth of hES cells in an undifferentiated state. Concentrations of FGF effective for promoting undifferentiated hES cell growth on their own usually have a lower bound of about 20, 30, or 40 ng/mL, with a practical upper bound of about 200, 500, or 1000 ng/mL. Concentrations of at least 60, 80, or 100 ng/mL bFGF are both reliable and cost effective. Equivalent concentrations of other forms and analogs of FGF can be determined empirically by weaning cultures from bFGF into the proposed substitute, and monitoring the culture for differentiation according to the marker system described below.

pPS cells expanded by another culture method (or obtained from a primary source) can be inoculated into a vessel adapted to keep the cells in suspension. The vessel walls may be typically inert or resistant to adherence of undifferentiated pPS cells. There may also be a means for preventing the cells from settling out, such as a stirring mechanism like a magnetically or mechanically driven stir bar or paddle, a shaking mechanism (typically attached to the vessel by the outside), or an inverting mechanism (i.e., a device that rotates the vessel so as to change the direction of gravity upon the cells). The use of any suitable agitation means is contemplated Vessels suitable for suspension culture for process development include the usual range of commercially available spinner or shaker flasks. Fermenters suitable for commercial production are Celligen Plus™ (New Brunswick Scientific Co.) and the Stirred-Tank Reactor™ (Applikon Inc.). Other suitable bioreactors include the Wave Bioreactor (GE Healthcare). These bioreactors can be continuously perfused with medium or used in a fed-batch mode, and come in various sizes.

Additional details regarding the propagation of pPS cells in suspension may be found in WO 07/002086.

Optimization of the suspension culture system can be accomplished by empirical testing. Undifferentiated cells from a previous surface or suspension culture can be passaged to the test condition, and cultured for a week or more. The cells can be examined periodically for characteristics of hES cells, for example, using the marker system described in the next section. The cells can also be passaged back to a well-established culture system, and evaluated for classic morphological features of undifferentiated cells as well as any of the markers associated with pluripotent stem cells described herein.

The hES cells used according to the present invention are intended ultimately for differentiation into cells of the chondrocyte lineage. The appropriate test to use during culture may not be the marker profile of the undifferentiated culture, but rather the ability of the cells to differentiate as required. The pluripotency of hES suspension cultures can be confirmed by sampling the cells, and either producing teratomas in SCID mice, or by staining EB-derived cells for markers representing all three germ layers. Markers for pluripotency include Oct4 and Nanog.

Alternatively or in addition, the suspension culture may contain particulate carriers that create surfaces within the suspension, but still provide the benefits of culturing the cells in a three-dimensional space. The cells are cultured and passaged in the same way, except that the particles are retained in the vessel during medium exchange, and more particles are added when the cells are split.

One type of microcarrier is solid spherical or semi-spherical particles made from glass, plastic, and dextran having a positive charge to augment cell attachment (Cytodex), and so on. Another type is disk-shaped culture plastic, such as the Fibra-cel Disks™ sold by New Brunswick Scientific Co, Inc. A gram of these disks provide a surface area of 1200 $cm^2$. Another type of microcarrier is macroporous particles of various pore sizes that permit the cells to reside in the interior as well as the outside, to potentially enhance the protective effect. In order to recover the hES cells with minimal disruption, it is beneficial to use particles made of a material such as agarose that can easily be dissolved or dispersed by gentle mechanical or enzymatic action, thereby releasing the cells for harvest or further culture. Solid carriers are optionally coated with an hES cell friendly extracellular matrix, such as laminin, Matrigel® or the like so that the attached cells have the same microenvironment as cells plated onto a solid surface.

Characteristics of Undifferentiated hES Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provide routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

hES cells can be characterized by expressed cell markers detectable by antibody (flow cytometry or immunocytochemistry) or by reverse transcriptase PCR. hES cells typically have antibody-detectable SSEA-3, SSEA-4, Tra-1-60, and Tra-1-81, but little SSEA-1, and have alkaline phosphatase activity. Panels of suitable markers detectable at the mRNA level are listed in US 2003/0224411. Exemplary are Cripto, gastrin-releasing peptide (GRP) receptor, podocalyxin-like protein (PODXL), human telomerase reverse transcriptase (hTERT), and the POU transcription factor Oct 3/4.

As already described, an important feature of propagated hES cells is a potential to differentiate into cells of all three germ layers: endoderm, mesoderm, and ectoderm. Pluripotency of hES cells can be confirmed by forming teratomas in SCID mice, and examining them for representative tissues of all three germ layers. Alternatively, pluripotency can be determined by allowing hES cells to differentiate non-specifically (for example, by forming embryoid bodies), and then determining the cell types represented in the culture by immunocytochemistry.

Standard Methods for Differentiating Pluripotent Cells or Chondrocyte Precursor Cells into Chondrocytes Chondrocytes can be obtained from DCCPC of this invention by culturing, differentiating, or reprogramming the chondrocyte precursor cells in a special growth environment that enriches for cells with the desired phenotype (either by outgrowth of the desired cells, or by inhibition or killing of other cell types). These methods are also applicable to many types of stem cells, including primate pluripotent stem (pPS) cells, including iPS cells, described herein.

When derived from an established line of pPS cells, the cell populations and isolated DCCPC of this invention will have the same genome as the line from which they are derived. Reference to the cells having the same genotype is not intended to imply that the cells cannot be genetically manipulated by the human hand (embodiments encompassing genetically altered cells are described infra), or that very minor changes (e.g., less than a fraction of a percent of the entire genome) might occur spontaneously (e.g. in the non-coding regions), but rather merely to suggest that the act of differentiating the cells from pPS cells into cells of the chondrocyte lineage will not, by itself, result in an altered genotype. Typically the genetic identity between a parental (undifferentiated cell) and its differentiated progeny will be similar to the genetic identity found between identical twins. Typically the pPS cell line and its DCCPC or chondrocyte progeny will share about 96%, about 97%, about 98%, about 99%, about 99.9% genetic identity.

The methods of the invention to prepare chondrocyte precursors cells do not require the formation of an embryoid body.

In certain embodiments the methods of the invention to prepare mature chondrocytes and/or cells expressing collagen II do not require the formation of a construct. In other embodiments the formation of a construct comprising chondrocyte progenitor cells may facilitate differentiation of the DCCPC into mature chondrocytes and/or cells expressing collagen II.

In order to direct the chondrocyte precursor cell culture towards the chondrocyte pathway, precursor cells that have been prepared as described above can be cultured in a cocktail of chondrocyte differentiation factors. Alone or in combination, each of the factors may direct cells to differentiate down the chondrocyte pathway, cause outgrowth of cells with a chondrocyte phenotype, inhibit growth of other cell types, or enrich for chondrocytes in another fashion: it is not necessary to understand the mechanism resulting in chondrocytes being enriched in order to practice the invention.

Components of the chondrocyte differentiation mix may include transforming growth factors (especially TGFβ1, TGFβ2 and TGFβ3), fibroblast growth factors (especially basic fibroblast growth factor, FGF-2), growth and differentiation factors (especially GDF-5, GDF-6 and GDF-7), bone morphogenic proteins (especially BMP-2, BMP-4, BMP-5, BMP-6 and BMP-7), hedgehog proteins (especially Indian hedgehog, IHH), L-ascorbic acid, and parathyroid hormone-related protein (PTHrP). Gibco is a preferred source of basic FGF. Most of the other compounds are available from R&D Systems, Minneapolis Minn.

Other ligands or antibodies that bind the same receptors can be considered equivalents to any of the receptor ligands referred to in this disclosure. Transforming growth factors beta (TGFβ) regulate various aspects of embryonic development and are expressed in the environment of sympathoadrenal progenitor cells (Wall et al., Curr. Opin. Genet. Dev. 4:517, 1994). In some systems, TGFβ regulates expression of parathyroid hormone-related protein (PTHrP) (Pateder et al., J. Cell Physiol. 188:343, 2001). BMPs and growth and differentiation factors (GDFs) are believed to play a central role during skeletogenesis, including joint formation (Francis-West et al., Cell Tissue Res 1296:111, 1999). Indian hedgehog (IHH) is an essential component of mechanotransduction complex to stimulate chondrocyte proliferation (Wu et al., J. Biol. Chem. 276:35290, 2001). During endochondral ossification, two secreted signals, IHH and PTHrP are believed to form a negative feedback loop regulating the onset of hypertrophic differentiation of chondrocytes. Bone morphogenetic proteins (BMP) are thought to be mediators of signalling pathways for the patterning of skeletal elements and mechanisms for the induction of cartilage and bone formation. (Hoffmann et al., Crit. Rev. Eukaryot. Gene Expr. 11:23, 2001). BMPs have been implicated as potential interactors of the IHH/PTHrP feedback loop (Minina et al., Development 128:4523, 2001). BMPs may very well interact with IHH and PTHrP to coordinate chondrocyte proliferation and differentiation.

Phenotypic Markers of Chondrocytes

Type II collagen and aggrecan can be used as specific markers for cells that model articular cartilage. Cultures can be screened for the absence of elastin and Type I collagen, markers of elastic cartilage and fibrocartilage, respectively. Cultures may also be screened for the absence of Type X collagen and osteocalcin, markers of hypertrophic cartilage and bone, respectively, which could indicate a transient chondrocyte phenotype generated during the progression of endochondral bone formation. A table of commercially available antibodies for these human markers is shown below (Table 2).

Tissue-specific markers can be detected using any suitable immunological technique, such as flow immunocytochemistry for cell-surface markers, or immunohistochemistry (for example, of fixed cells or tissue sections) for intracellular or cell-surface markers. A detailed method for flow cytometry analysis is provided in Gallacher et al., Blood 96:1740, 2000. Expression of a cell-surface antigen is defined as positive if a significantly detectable amount of antibody will bind to the antigen in a standard immunocytochemistry or flow cytometry assay, optionally after fixation of the cells, and optionally using a labelled secondary antibody or other conjugate to amplify labelling. A significantly detectable amount of antibody may for example be an amount in excess when compared to an isotype antibody control to an irrelevant epitope. Possible sources of specific antibody are shown in Table 2.

TABLE 2

Commercial Sources of Antibody to Connective Tissue Markers

| Antibody | Source |
| --- | --- |
| Type I collagen | Chemicon, cat. # AB758 |
| Type II collagen | Chemicon, cat # AB761 |
| Type X collagen | RDI, cat # RDI-COLL10abr |
| Elastin | Chemicon, cat # AB2043 |
| Osteocalcin | Biomed. Tech. Inc., cat # BT593 |
| Aggrecan | BioTrend, cat # 0195-8050 |

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Real time PCR may also be performed using commercially available systems such as TaqMan® (Applied Biosystems). Sequence data for particular markers listed in this disclosure can be obtained from public databases such as GenBank.

To facilitate engraftment, it is beneficial to maximize the proportion of cells in the population that have the characteristics of chondrocytes or their precursors, such as DCCPC, by refining the mixture of differentiation factors, culture conditions, and timing and following these markers. Populations in which at least 5% of the cells synthesize either Type II collagen or aggrecan, or both, may well be suitable. Populations enriched to the point where at least 25% of the cells synthesize either Type II collagen or aggrecan would be more efficacious in a number of contexts.

For therapeutic applications relating to cartilage regeneration, it may be desirable to minimize the ability of the cell population to form elastic cartilage, fibrocartilage, hypertrophic cartilage and bone. This means that the proportion of cells synthesizing Type I collagen, Type X collagen, or osteocalcin (alone or in combination) is as low as possible, preferably below $115^{th}$ of the cells staining positive for Type II collagen or aggrecan, or less than 1%. Also desirable are populations with a low residual proportion of undifferentiated pPS cells. Preferred populations are less than 1%, or 0.2% SSEA-4 positive (+ve), Oct-4 positive (+ve), or positive for expression of endogenous telomerase reverse transcriptase. Any depletion technology known in the art may be used eliminate unwanted cell populations. For example magnetic beads conjugated with antibodies specific to an extra-cellular marker may be used.

Animal Model Experiments

Of considerable interest for development of chondrocytes for clinical application is the ability of cell populations to model cartilage and restore joint function in a host. Reconstitution of chondrocyte function can be tested using several well-established animal models.

Pilot experiments can be conducted using a model in which 6 mm holes are put in the external ear of the rabbit, leaving the adherent skin intact. Matrixes seeded with chondrocytes are then implanted, and the animals are monitored for hole closure (ten Koppel et al., Biomaterials 22:1407, 2001).

Alternatively, full thickness defects can be created in the weight bearing surface of the medial femoral chondyle of femora in rabbits (Grigolo et al., Biomaterials 22:2417, 2001). The full-thickness defect allows blood to seep into the site from the marrow cavity, creating a clot that contains endogenous stem cells.

Alternatively, partial thickness defects that do not puncture the subcutaneous bone can be created Nehrer et al., (Biomaterials 19:2313-2328, 1998) (Hunziker et al., Clin. Orthop. 391 Supp:S171, 2001). Partial thickness defects more accurately model acute cartilage defects due to trauma. In this model the spontaneous healing component of innate cartilage repair is reduced and endogenous stem cells contribute little to cartilage regrowth.

The wounds are repaired using chondrocytes seeded on a biomaterial, injected as single cells or used as a multicellular aggregate from the construct culture. A biological membrane such as a piece of the periosteum or facia may be used to hold the implant in place. Alternatively synthetic matrices such as vicryl or polydioxanone meshes may be used. Matrix-cell implants can also be held in place with surgical dart.

Rather than the medial chondyle, the work can be done with a defect created in the trochlear groove. This is a non-weight-bearing site, and implants are not dislodged as easily as from the medial chondyle.

Histologic samples from the treatment site are examined 1-6 months after surgery for population with the implant cells and cartilage deposits. This includes immunostaining for Type II collagen and aggrecan. Important morphological characteristics of the implant include cartilage thickness, smooth articular surface, intact or reconstituted cement line and integration of the implant and endogenous cartilage at the borders of the defect. Long-term stability of the implant can be verified at the 12 month point.

As another option, osteoarthritis can be modelled by the injection of estradiol into the knee joint of ovarectomized rabbits, causing loss of condyle surface congruity that resemble the defects observed in osteoarthritis in humans (Tsai et al., Clin Orthoop. 291:295, 1993). Alternatively joint destabilisation via transaction of supportive ligaments may be used to model osteoarthritis (Glasson S., OsteoArthritis and Cartilage (2007) 15, 1061-1069).

Other mammals may be used as an animal model. Suitable mammals include rodents such as rats and mice, ungulates such as pigs, sheep cows and horses, felines, canines and non-human primates.

Animal models described above may also be used to investigate acceptance or rejection of implanted cells. Accordingly evidence of immune rejection may be investigated. Evidence of immune rejection may include leukocyte infiltration into the implant site, evidence of inflammation such as the presence of pro-inflammatory cytokines. Loss of implanted cells may also suggest immune rejection. Other signs of immune rejection may include lymphocyte proliferation and stimulation of interferon gamma production.

Genetic Modification of Differentiated Cells

Certain chondrocyte precursor cell populations of this invention, such as DCCPC have a substantial proliferation capacity. If desired, the replication capacity can be further enhanced by increasing the level of telomerase reverse transcriptase (TERT) in the cell, either by increasing transcription from the endogenous gene, or introducing a transgene. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999. Genetically altered cells can be assessed for hTERT expression by RT-PCR, telomerase activity (TRAP assay), immunocytochemical staining for hTERT, or replicative capacity, according to standard methods. Other methods of immortalizing cells are also contemplated, such as transforming the cells with DNA encoding myc, the SV40 large T antigen, or MOT-2 (U.S. Pat. No. 5,869,243, WO 97/32972 and WO 01/23555).

If desired, the cells of this invention can be prepared or further treated to remove undifferentiated cells in vitro, or to safeguard against revertants in vivo. One way of depleting undifferentiated stem cells from the population is to transfect the population with a vector in which an effector gene under control of a promoter that causes preferential expression in undifferentiated cells—such as the TERT promoter or the OCT-4 promoter. The effector gene may be a reporter to guide cell sorting, such as green fluorescent protein. The effector may be directly lytic to the cell, encoding, for example, a toxin, or a mediator of apoptosis, such as caspase (Shinoura et al., Cancer Gene Ther. 7:739, 2000). The effector gene may have the effect of rendering the cell susceptible to toxic effects of an external agent, such as an antibody or a prodrug. Exemplary is a herpes simplex thymidine kinase (tk) gene, which causes cells in which it is expressed to be susceptible to ganciclovir (WO 02/042445). Alternatively, the effector can cause cell surface expression of a foreign determinant that makes any cells that revert to an undifferentiated phenotype susceptible to naturally occurring antibody in vivo (WO 02/042445). Other ways of eliminating unwanted pluripotent cells include using immuno-precipitating reagents such as a bead conjugated with an antibody to a cell surface protein expressed on a pluripotent stem cell.

Uses of Propagated Chondrocyte Cells

This invention provides a method by which large numbers of chondrocyte or DCCPC can be produced on a commercial scale from pPS cells, in particular hES cells. The chondrocyte or DCCPC are useful for a number of research and commercial purposes.

Therapeutic Uses

This invention also provides for the use of DCCPC and their derivatives to treat conditions leading to impairment of joint mobility or defects or depletions relating to the in vivo functional capability of endogenous cartilage. Suitable subjects include any mammal such as a rat, a mouse, a rabbit, a pig, a cow, a horse, a sheep, a cat, a dog, a non-human primate such as a chimpanzee or a macaque, and a human.

Included is damage caused by percussive trauma, and sports injuries. The cells of the invention can also be considered for treatment of degenerative conditions, such as osteoarthritis and rheumatoid arthritis to restore lost function, providing that the primary pathology causing the degeneration is sufficiently well controlled. Also contemplated is the use of the cells of this invention for cosmetic surgery, including but not limited to ear, spine and nasal surgery (i.e. of the proboscis). See *Aesthetic Reconstruction of the Nose*, by G. C. Burget & F. J. Menick, Mosby Year Book 1994; *The Nose*, by Nikolay Gogol et al., David R. Godine publisher, 1993; and Yoo et al., J. Urol. 162:1119, 1999.

DCCPC and/or chondrocytes made according to this invention can be prepared for administration in a cell suspension (using trypsin or collagenase, if necessary), using a physiologically compatible excipient: for example, an isotonic medium containing 1.25 mL gentomycin sulfate (70 µmol/L), 2.0 mL amphotericin (2.2 µmol/L), 7.5 mL L-ascorbic acid (300 µmol/L), 25 mL blood serum or its equivalent (to 10% vol/vol) in 300 mL. During the cell transplantation procedure, the damaged cartilage can be covered with a cap secured by mechanical or adhesive retention means, such as a biocompatible fibrin glue. The cultured cells in transplant excipient (about 0.6 mL containing about $10 \times 10^6$ chondrocytes) may then be injected under the covering cap using a ~23 gauge needle.

Alternatively, the DCCPC and/or chondrocytes can be prepared by growing the cells on a matrix formed, for example, using a collagen membrane (commercially available collagen matrix pads are available from Ed. Geistlich Sohne, Switzerland). A few days before transplant, the growth media is exchanged for a transplant excipient. During surgery, the cell-loaded matrix is glued into the area of damaged cartilage using a biocompatible adhesive. The covering cap or matrix remains in place for a period of time sufficient to allow for cartilage repair, and is then absorbed or resorbed by the body, for example, within two to three months from implantation. Further elaboration of the design and use of resorbable caps and matrices can be found in International patent publication WO 01/08610.

Patient selection, mode of administration, and choice of support structures and surgical options is within the skill of the managing clinician.

For purposes of commercial distribution, chondrocytes of this invention are typically supplied in the form of a pharmaceutical composition, comprising an isotonic excipient prepared under sufficiently sterile conditions for human administration. For general principles in medicinal formulation of cell compositions, the reader is referred to *Cell Therapy: Stem Cell Transplantation, Gene Therapy, and Cellular Immunotherapy*, by G. Morstyn & W. Sheridan eds, Cambridge University Press, 1996. The composition may also contain a matrix for keeping the chondrocytes in place during the first few months following therapy. Absorbable biomaterials save the necessity of subsequent surgical removal. Besides the collagen matrix pads described in WO 01/086101, other possible matrixes include bioresorbable polymer fleece matrices (Rudert et al., Cells Tissues Organs 167:95, 2000); hyaluronan derivatives (Grigolo et al., Biomaterials 22:2417, 2001); sponge made from poly(L-lactide-epsilon-caprolactone) (Honda et al., J. Oral Maxillofac. Surg. 58:767, 2000), and collagen-fibrin matrices (Clin. Exp. Rheumatol. 18:13, 2000).

Screening Uses

The chondrocytes or DCCPC can be used to screen for factors (such as small molecule drugs, peptides, polynucleotides, and the like) or conditions (such as culture conditions or manipulation) that affect the characteristics of chondrocytes or DCCPC in culture. Such cultures can also be used for the testing of pharmaceutical compounds in drug research. Assessment of the activity of candidate pharmaceutical compounds generally involves combining the differentiated cells of this invention, such as chondrocytes or DCCPC with the candidate compound, determining any resulting change, and then correlating the effect of the compound with the observed change. Comparisons can be made to an equivalent culture that has not been treated with the factor or compound. Cytotoxicity or metabolic effects can be determined by cell viability, morphology, the expression or release of certain markers, receptors or enzymes, DNA synthesis or repair, and so on. The cells prepared according to the present invention can be used for drug screening, preparing pharmaceutical compositions, research, and many other similar purposes.

In one example, the DCCPC can be used to screen factors that promote maturation into chondrocytes, or promote proliferation and maintenance of chondrocytes in long-term culture. For example, candidate maturation factors or growth factors can be tested by adding them to cells in different wells, and then determining any phenotypic change that results (such as expression of collagen II and/or aggrecan), according to desirable criteria for further culture and use of the cells. Comparisons can be made to an equivalent culture that has not been treated with the factor. This can lead to improved derivation and culture methods not only for pPS derived chondrocytes, but for chondrocytes and their progenitors isolated from cartilage.

Another example is the use of DCCPC to measure the effect of molecules capable promoting chondrocyte survival under conditions of stress. For example those associated with trauma through injury, surgery or osteoarthritis.

Another example is the use of chondrocyte precursors to measure the effect of small molecule drugs that have the potential to affect chondrocyte activity in their role of shaping or remodelling cartilage. To this end, the cells can be combined with test compounds in vitro, and the effect of the compound on gene expression or protein synthesis can be determined. The screening can also be done in vivo by measuring the effect of the compound on the behaviour of the cells in an animal model. Untreated cells or animals may be used for comparison.

Other screening methods of this invention relate to the testing of pharmaceutical compounds for a potential effect on chondrocyte growth, development, or toxicity. This type of screening is appropriate not only when the compound is designed to have a pharmacological effect on chondrocytes themselves, but also to test for chondrocyte-related side-effects of compounds designed for a primary pharmacological effect elsewhere.

Assessment of the activity of candidate pharmaceutical compounds generally involves combining the differentiated cells of this invention with the candidate compound, either alone or in combination with other drugs ("In vitro Methods in Pharmaceutical Research", Academic Press, 1997; and U.S. Pat. No. 5,030,015). The investigator determines any change in the morphology, marker phenotype, or functional activity of the cells that is attributable to the compound (compared with untreated cells or cells treated with an inert compound), and then correlates the effect of the compound with the observed change. Untreated cells may be used for comparison.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread (A. Vickers, pp 375-410 in "In vitro Methods in Pharmaceutical Research," Academic Press, 1997).

Commercial Distribution

Components of the chondrocyte differentiation culture system of this invention may be prepared together in various useful combinations, such as two or more of the following:

media suitable for culturing DCCPC and/or chondrocytes in suspension or adherently extracellular matrix components or thickeners present in or to be added to the medium or coated onto a suitable cell growth surface microcarriers present in or to be added to the medium vessels adapted for suspension culture or adherent culture the chondrocytes or DCCPC themselves, either growing in a culture system, or stored in another form, but intended for use in a culture system pPS cells in culture or stored in a suitable excipient or buffer one or more cytokines, growth factors, morphogens or the like suitable for promoting the growth, differentiation and/or maturation of pPS cells and/or chondrocyte precursor cells into mature chondrocytes The products and product combinations may be packaged in suitable containers, optionally in kit form, and may be accompanied by written information on the use of the materials according to this invention—such as maintaining or expanding chondrocyte cells. The written information may take the form of a label on the container or the kit, or a product insert packaged with the container and distributed together. Equivalent forms are descriptions, instructions, or explanations written in hard copy or in electronic form available to the user or the intended user as reference or resource material associated with the commercially distributed product.

This invention may also include sets of cells and other components that exist at any time during their manufacture, distribution, or use. The cell sets can comprise any combination of two or more cell populations described in this disclosure, exemplified but not limited to a type of differentiated pPS-derived chondrocyte precursor cell prepared by a method of the invention, such as DCCPC in combination with undifferentiated pPS cells or other differentiated cell types (e.g. fully differentiated chondrocytes), sometimes sharing the same genome. Each cell type in the set may be packaged together, or in separate containers. The products of this invention are optionally packaged in a suitable container or kit with written instructions for a desired purpose, such as the treatment of a cartilage defect, the reconstruction of joint cartilage or cosmetic surgery.

The present invention has shown that ES cells differentiated for 14 days in chondrogenic media are able to revert to a dedifferentiated state (DCCPC) if the differentiation factors present in the media are removed. Cells de-differentiated are valuable for a number of reasons: 1) the initial differentiation step using the chondrogenic protocol described herein is effective at removing or differentiating pluripotent cells, thus limiting their ability to form teratomas; 2) de-differentiation allows the cells to proliferate and provide a second bulking up stage; and 3) the de-differentiated cells from primary chondrocytes have been shown to be plastic adherent and will passage as single cells (unlike hESCs). The de-differentiated cells are stable and can be subsequently differentiated into collagen II expressing cells and/or mature chondrocytes either under adherent conditions or when grown in suspension as a construct. These features are highly beneficial to large scale production of a cell therapy.

Additional Embodiments of the Invention

1. Cell Cultures and Cell Populations

In some embodiments the invention provides a cell culture comprising a population of cells wherein the population of cells are the in vitro progeny of pPS cells and wherein the population of cells express CBFA1/RunX2, and are Ki67 negative and negative for pluripotency markers Tra 1-60, Oct 4 and nanog. The cell population may also be negative for pluripotency markers SSEA 3 and SSEA 4.

In certain embodiments the cell culture never comprises an embryoid body. In some embodiments the cell culture comprises only adherent cells. In some embodiments the culture does not comprise a construct. In other embodiments the cell culture may comprise a construct of cells.

In some embodiments of the invention the cell culture comprises cells wherein more than 10%, more than 20%, more than 30%, more than 40%, more than 50%, more than 60%, more than 70%, more than 80% of the cells in the cell culture express CBFA1/RunX2. In some embodiments of the invention 85% of the cells in the population express CBFA1/RunX2.

In some embodiments of the invention the cell culture comprises cells wherein less than 20%, less than 10%, less than 5%, less than 2%, less than 1% of the cells in the cell culture express one or more of the following markers: Tra 1-60, Oct 4, nanog, SSEA4, SSEA 3 and Ki67. In other embodiments of the invention none of the cells in the cell culture are detectible for at least one of the following markers: Tra 1-60, Oct 4, nanog, SSEA4, SSEA 3 and Ki67.

In some embodiments the cell culture is provided on a surface such that the cells are in direct contact with a plastic surface e.g. a plastic tissue culture dish. In other embodiments the culture is provided on substrate that coats a tissue culture surface. In some embodiments the substrate may be comprised of one or more extra cellular matrix components. In some embodiments the substrate may be comprised of laminin. In some embodiments the substrate may comprise the extract of a murine sarcoma cell, e.g. Matrigel®. In some embodiments the substrate is not collagen. In some embodiments the substrate is not gelatin.

In some embodiments the cell culture comprises a nutrient media. The nutrient media may be comprised of serum such as fetal calf serum or the like. In some embodiments the media may be comprised of about 5-20% serum. In some embodiments the media is comprised of 10% serum. In some embodiments the nutrient media is a commercially available media such as DMEM. In other embodiments the cell culture comprises a dedifferentiation media, e.g. a media that is 10% FBS such as DMEM (Invitrogen). In some embodiments the nutrient media does not comprise exogenously added TGFβ1, FGF2, and PDGFbb beyond what is found in a media comprising 10% FCS.

2. Systems for Producing Chondrocyte Lineage Cells

In certain embodiments the invention provides a system for producing chondrocyte lineage cells. Chondrocyte lineage cells may include mature chondrocytes, DCCPC, and/or cells expressing one or more of the following: collagen II, aggrecan, glycosamino-glycan.

The system for producing chondrocyte lineage cells may comprise 1) a first population of cells comprising pPS cells and 2) a second population of cells comprising DCCPC wherein the DCCPC are the in vitro progeny of a portion of the pPS cells.

In further embodiments the invention provides a system for producing chondrocyte lineage cells comprising 1) a first population of cells comprising pPS cells and 2) a second population of cells comprising cells that express CBFA1/RunX2 and do not express Ki67, wherein the cells expressing CBFA1/RunX2 without expressing the proliferation marker Ki67 are the in vitro progeny of a portion of the pPS cells.

Because pPS cells may be established as cell lines and thus grown continuously in culture while maintaining their pluripotent state they can produce chondrocyte lineage cells in virtually unlimited supply. The chondrocyte lineage cells produced will be essentially genetically identical to the parent pPS cell line. Thus the system provides for a continual unlimited source of chondrocyte lineage cells that are essentially genetically identical to one another.

In some embodiments the system is never comprised of an embryoid body. In some embodiments the system is never comprised of a construct. In some embodiments the cells are maintained adherently throughout (except for the time required for passaging e.g. trypsinization or the like). In some embodiments of the invention one or both populations of cell populations comprising the system may be provided on a plastic surface such as the surface of a cell culture article. In other embodiments of the invention one or both of the cell populations comprising the system are provided on a substrate that coats a tissue culture surface. In some embodiments the substrate may be comprised of one or more extra cellular matrix components. In some embodiments the substrate may be comprised of laminin. In some embodiments the substrate may comprise the extract of a murine sarcoma cell, e.g. Matrigel®. In some embodiments the substrate is not collagen. In some embodiments the substrate is not gelatin. In other embodiments the second population of cells may be provided as a construct. The construct may be provided as a non-adherent cell population, e.g. a cell population that is not attached to either a plastic surface or an exogenously provided substrate such as a cell matrix. The cells of the construct may be attached to other cells within the construct.

In some embodiments of the invention the system may further comprise one or more nutrient media. In certain embodiments of the invention the first population of cells is provided in a media comprising one or more of the following: linoleic acid and bovine serum albumin. In some embodiments the media may further comprise one or more of the following: dexamethasone, insulin, transferrin, selenium, ascorbic acid, sodium pyruvate, and transforming growth factor β (TGFβ), e.g. TGFβ3. In certain embodiments the media does not comprise an exogenously added bone morphogenic protein. In certain embodiments the media does not comprise a serum replacement such as knock out serum replacement.

A suitable media concentration of linoleic acid may range from about 2 mg/ml to about 10 mg/ml; from about 3 mg/ml to about 7 mg/ml; from about 4 mg/ml to about 6 mg/ml. In one embodiment of the invention the media is comprised of about 5.35 mg/ml of linoleic acid. A suitable media concentration of bovine serum albumin may range from about 0.5 mg/ml to about 5 mg/ml; from about 0.8 mg/ml to about 3 mg/ml; from about 1 mg/ml to about 2 mg/mi. In one embodiment of the invention the media is comprised of about 1.25 mg/ml of bovine serum albumin. A suitable media concentration of dexamethasone may range from about $10^{-8}$M to about $10^{-6}$; from about $10^{-7}$ M to about $10^{-6}$M, from about $10^{-8}$M to about $10^{-7}$ M. In one embodiment of the invention, the media is comprised of about $10^{-7}$ M dexamethasone. A suitable media concentration of insulin may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml insulin. A suitable media concentration of transferrin may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml transferrin. A suitable media concentration of selenious acid may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml selenious acid. A suitable media concentration of proline may range from about 20 μg/ml to about to about 80 μg/ml; from about 30 μg/ml to about 70 μg/ml; from about 40 μg/ml to about 60 μg/ml. In one embodiment of the invention the is comprised of about 40 μg/ml of proline. A suitable media concentration of ascorbic acid may range from about 30 μg/ml to about 90 μg/ml; from about 40 μg/ml to about 80 μg/ml; from about 45 μg/ml to about 60 μg/ml. In one embodiment of the invention the media is comprised of about 50 μg/ml of ascorbic acid. A suitable media concentration of TGFβ may range from about 1 ng/ml to about 30 ng/ml; from about 5 ng/ml to about 20 ng/ml; from about 8 ng/ml to about 15 ng/ml. In one embodiment of the invention the media is comprised of about 10 ng/ml of TGFβ.

In some embodiments of the invention the second population of cells is provided in a nutrient media such as a commercially available media, e.g. DMEM (Invitrogen). In some embodiments the nutrient media does not comprise exogenously added TGFβ3, FGF2, and PDGFbb beyond what is found in a media comprising 10% FCS.

In some embodiments the second population of cells is provided in a nutrient media comprising serum. The nutrient media may be comprised of serum such as fetal calf serum or the like. In some embodiments the media may be comprised of about 5-20% serum. In some embodiments the media is comprised of 10% serum. In some embodiments the nutrient media is a commercially available media such as DMEM. In other embodiments the cell culture comprises a dedifferentiation media, e.g. a media that is 10% FBS such as DMEM (Invitrogen).

In some embodiments of the invention the second population of cells may be transferred from a nutrient media comprising 10% serum to the media used for culturing the first population of cells.

3. Methods for Producing Dedifferentiated Committed Chondrocyte Progenitor Cells (DCCPCs)

In certain embodiments the invention provides a method of producing (DCCPCs) comprising 1) culturing pPS cells in a chondrogenic media and 2) removing the chondrogenic media and substituting a dedifferentiation media in its place.

In other embodiments the invention provides a method of producing a cell that expresses CBFA1/RunX2 comprising) culturing pPS cells in a chondrogenic media and 2) removing the chondrogenic media and substituting a dedifferentiation media in its place. The cells expressing CBFA1/RunX2 may be negative for Ki67. The cells expressing CBFA1/RunX2 may be negative for one or more of the following markers Oct4, nanog, SSEA4, SSEA3, TRA-1-60. The cells expressing CBFA1/RunX2 may have a fibroblast like morphology.

In certain embodiments of the invention the chondrogenic media comprises one or more of: linoleic acid and bovine serum albumin. The media may further comprise one or more of the following: dexamethasone, insulin, transferrin, selenium, ascorbic acid, sodium pyruvate, and transforming growth factor β (TGFβ), e.g. TGFβ3. In certain embodiments the media does not comprise an exogenously added bone morphogenic protein. In certain embodiments the media does not comprise a serum replacement such as knock out serum replacement.

A suitable media concentration of linoleic acid may range from about 2 mg/ml to about 10 mg/ml; from about 3 mg/ml to about 7 mg/ml; from about 4 mg/ml to about 6 mg/ml. In one embodiment of the invention the media is comprised of about 5.35 mg/ml of linoleic acid. A suitable media concentration of bovine serum albumin may range from about 0.5 mg/ml to about 5 mg/ml; from about 0.8 mg/ml to about 3 mg/ml; from about 1 mg/ml to about 2 mg/ml. In one embodiment of the invention the media is comprised of about 1.25 mg/ml of bovine serum albumin. A suitable media concentration of dexamethasone may range from about $10^{-8}$M to about $10^{-6}$, from about $10^{-7}$ M to about $10^{-6}$M; from about $10^{-8}$ M to about $10^{-7}$ M. In one embodiment of the invention the media is comprised of about $10^{-7}$ M dexamethasone. A suitable media concentration of insulin may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml insulin. A suitable media concentration of transferrin may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml transferrin. A suitable media concentration of selenious acid may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml selenious acid. A suitable media concentration of proline may range from about 20 μg/ml to about to about 80 μg/ml; from about 30 μg/ml to about 70 μg/ml; from about 40 μg/ml to about 60 μg/ml. In one embodiment of the invention the is comprised of about 40 μg/ml of proline. A suitable media concentration of ascorbic acid may range from about 30 μg/ml to about 90 μg/ml; from about 40 μg/ml to about 80 μg/ml; from about 45 μg/ml to about 60 μg/ml. In one embodiment of the invention the media is comprised of about 50 μg/ml of ascorbic acid. A suitable media concentration of TGFβ may range from about 1 ng/ml to about 30 ng/ml; from about 5 ng/ml to about 20 ng/ml; from about 8 ng/ml to about 15 ng/ml. In one embodiment of the invention the media is comprised of about 10 ng/ml of TGFβ.

In some embodiments of the invention the dedifferentiation media comprises a commercially available media, e.g. DMEM (Invitrogen). The media may be comprised of serum such as fetal calf serum (FCS). In certain embodiments the media is about 10% FCS. In some embodiments the media does not comprise exogenously added TGFβ1, FGF2, and PDGFbb beyond what is found in a media comprising 10% FCS.

In some embodiments of the invention the method of producing DCCPCs comprises culturing the pPS cells adherently. In some embodiments of the invention the pPS cells never form an embryoid body. In certain embodiments of the invention the method may further comprise removing the cells from the adherent surface after they have been cultured in the chondrogenic media, pelleting the cells, e.g. by centrifugation, resuspending the cells in the dedifferentiation media (and filtering the cells to form a single cell suspension) and replating the cells on a new adherent surface in the dedifferentiation media.

In some embodiments of the invention step 1) of the method of making DCCPCs results in differentiating the pPS cells down the chondrocyte lineage pathway. Accordingly, step 1) comprises a method of differentiating pPS cells into cells of the chondrocyte lineage. Cells of the chondrocyte lineage may express one or more of the markers chosen from collagen II, collagen I, collagen X, aggrecan. Cells of the chondrocyte lineage may have a rounded morphology.

4. Methods of Producing Chondrocyte Lineage Cells and Chondrocytes

In some embodiments the invention provides a method for producing a chondrocyte comprising 1) obtaining an DCCPC and 2) differentiating the DCCPC into a chondrocyte.

In other embodiments the invention provides a method of producing a cell expressing one or more of the following markers: collagen II, aggrecan, and GAGs comprising 1) obtaining an DCCPC and 2) differentiating the DCCPC into a cell expressing one or more of the following markers: collagen II, aggrecan, GAGs.

In some embodiments the DCCPC may obtained by making DCCPCs according to any of the methods described infra. In other embodiments the DCCPC may be acquired from an individual or entity that has produced it.

In some embodiments the DCCPC are differentiated into chondrocytes by culturing the cells in a chondrogenic media for a suitable length of time. In other embodiments the DCCPC are differentiated into cells expressing one or more of the following markers: collagen II, aggrecan, GAGs, by culturing the cells in a chondrogenic media for a suitable length of time.

In some embodiments of the invention the DCCPC are first grown in a dedifferentiation media. To begin differentiating the cells according to step 2) the cells are switched to a chondrogenic media. Switching the media may include a step in which the cells are passaged, e.g. removed from an adherent surface with a suitable compound or combination of compounds such as trypsin, pelleted by centrifugation, and resuspended in the chondrogenic media and replated on an adherent surface or maintained in suspension as a construct of cells in the chondrogenic media. In other embodiments the cells are not passaged. Instead the cells remain attached to an adherent surface and the media is decanted. Optionally the cells may be washed with an appropriate buffer such as PBS and then fed with the chondrogenic media.

A chondrogenic media may comprise one or more of: linoleic acid and bovine serum albumin. The media may further comprise one or more of the following: dexamethasone, insulin, transferrin, selenium, ascorbic acid, sodium pyruvate, and transforming growth factor β (TGFβ) e.g. TGFβ3. In certain embodiments the media does not comprise an exogenously added bone morphogenic protein. In certain embodiments the media does not comprise a serum replacement such as knock out serum replacement.

A suitable media concentration of linoleic acid may range from about 2 mg/ml to about 10 mg/ml; from about 3 mg/ml to about 7 mg/ml; from about 4 mg/ml to about 6 mg/ml. In one embodiment of the invention the media is comprised of about 5.35 mg/ml of linoleic acid. A suitable media concentration of bovine serum albumin may range from about 0.5 mg/ml to about 5 mg/ml; from about 0.8 mg/ml to about 3 mg/ml; from about 1 mg/ml to about 2 mg/ml. In one embodiment of the invention the media is comprised of about 1.25 mg/ml of bovine serum albumin. A suitable media concentration of dexamethasone may range from about $10^{-8}$M to about $10^{-6}$; from about $10^{-7}$ M to about $10^{-6}$M; from about $10^{-8}$M to about $10^{-7}$ M. In one embodiment of the invention, the media is comprised of about $10^{-7}$ M dexamethasone. A suitable media concentration of insulin may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml insulin. A suitable media concentration of transferrin may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml transferrin. A suitable media concentration of selenious acid may range from about 3 ng/ml to about 20 ng/ml; from about 5 ng/ml to about 15 ng/ml; from about 6 ng/ml to about 9 ng/ml. In one embodiment of the invention the media is comprised of about 6.25 ng/ml selenious acid. A suitable media concentration of proline may range from about 20 µg/ml to about to about 80 µg/ml; from about 30 µg/ml to about 70 µg/ml; from about 40 µg/ml to about 60 µg/ml. In one embodiment of the invention the is comprised of about 40 µg/ml of proline. A suitable media concentration of ascorbic acid may range from about 30 µg/ml to about 90 µg/ml; from about 40 µg/ml to about 80 µg/ml; from about 45 µg/ml to about 60 µg/ml. In one embodiment of the invention the media is comprised of about 50 µg/ml of ascorbic acid. A suitable media concentration of TGFβ may range from about 1 ng/ml to about 30 ng/ml; from about 5 ng/ml to about 20 ng/ml; from about 8 ng/ml to about 15 ng/ml. In one embodiment of the invention the media is comprised of about 10 ng/ml of TGFβ.

A suitable length of time for culturing the DCCPC in a chondrogenic media may range from about 4-28 days; from about 5-25 days; from about 7-21 days. In some embodiments the DCCPC are cultured in chondrogenic media for about 7 days; for about 10 days; for about 15 days; for about 21 days; for about 25 days. In one embodiment the DCCPCs are cultured in chondrogenic media for 21 days.

In some embodiments of the invention the method of producing chondrocytes comprises culturing the DCCPC adherently. In some embodiments of the invention the method of producing cells expressing one or more of the following markers: collagen II, aggrecan, GAGs; comprises culturing the DCCPC adherently. In some embodiments of the invention the DCCPC are obtained without ever forming an embryoid body. In some embodiments of the invention the cells are maintained adherently throughout the method (it is understood that the cells may be removed from the adherent surface briefly for passaging, but otherwise are maintained adherently).

In some embodiments the method comprises a step of forming a construct. A construct may be formed by removing the cells from an adherent surface and pelleting the cells, e.g. by centrifugation. For example a construct of DCCPC may be formed and placed in chondrogenic media in carrying out step 2). In other embodiments the method may not include a step of forming a construct of cells. A suitable number of cells for forming a construct may range from about 100,000 cells to about 600,000 cells; from about 200,000 cells to about 500,000 cells; from about 250,000 cells to about 350,000 cells. In one embodiment about 250,000 cells are used to form the construct.

In some embodiments culturing DCCPC adherently may include culturing them on a plastic tissue culture surface. In other embodiments of the invention culturing DCCPC adherently may include culturing the DCCPC on a substrate. The substrate may comprise extra cellular matrix components. In some embodiments the substrate may comprise laminin. In some embodiments the substrate may comprise an extract from a murine sarcoma cell, e.g. Matrigel®. In some embodiments the substrate is not collagen. In some embodiments the substrate is not gelatin. In some embodiments both step 1) and step 2) of the method are performed on cells attached to an adherent surface. In other embodiments the DCCPC are obtained from an adherent surface, but step 2) is performed while the cells are in suspension, e.g. in the form of a construct.

5. Methods of Administering Cell Compositions to a Subject

In certain embodiments the invention provides a method of administering a cellular composition comprising a chondrocyte lineage cell to subject such that the cellular composition engrafts in the subject without generating an immune response to the cellular composition that would reject the engrafted cellular composition comprising 1) obtaining a cellular composition comprising chondrocyte lineage cell and 2) administering the chondrocyte lineage cell to the subject without administering an immuno-modulatory compound to the subject. Suitable chondrocyte lineage cells may include for example a mature chondrocyte, an DCCPC, a cell expressing one or more of the following markers: collagen II, aggrecan, GAGs. In other embodiments immunosuppressant drugs may, though, be co-administered subsequently, simultaneously or separately as appropriate.

In certain embodiments the chondrocyte lineage cells are maintained as a graft without generating an immune response for about 10 days, about 30 days, about 60 days, about 90 days, about 180 days, about one year. In other embodiments the chondrocyte lineage cells are maintained as a graft without generating an immune response for more than a month, more than 3 months, more than 6 months, more than a year.

The chondrocyte lineage cell may be administered to any site in need of cartilage repair or restoration. As an example the cells may be administered to an arthritic joint or a site that has suffered acute injury (FIG. 4). Such procedures using chondrocytes to repair a patient's knee cartilage are known in the art. For example, the CARTICEL™ autologous chondrocyte implantation (ACI) procedure involves taking a sample of cartilage from a low weight bearing location and expanding the explanted chondrocytes in vitro. In a later surgery a periosteal patch is sutured to the surface of the cartilage defect and the cultured chondrocyte preparation is injected under the patch and filling the defect.

As described above, the chondrocyte lineage cell preparation may be administered without an immuno-modulatory compound such as an immuno suppressant typically administered with cell grafts. Alternatively, such compounds may be used as appropriate. Examples of immuno-suppressants include cyclosporin, FK-506 and examples of immuno-modulatory compounds are anti-inflammatory agents such as steroidal compounds, e.g. prednisone and the like.

The administered cell composition may be allogeneic with respect to the subject. The administered cell composition may be xenogeneic with respect to the subject. Thus in some embodiments the cell composition will be a complete or partial mismatch with respect to one or more alleles of the major histocompatibility complex, such as MHC I and/or MHC II. In some embodiments the cell composition may be syngeneic with the subject. Suitable subjects include any mammal, e.g. a mouse, a rat, a dog, a cat, a cow, a horse, a sheep, a pig, a non-human primate, a human.

The cell composition may be administered surgically to the site. Alternatively the cell composition may be administered to the site by injection or through the use of arthroscopic techniques.

In certain embodiments the cell composition may range from about $1 \times 10^4$ cells to about $1 \times 10^8$ cells. In some embodiments about $1 \times 10^4$ cells may be administered to the subject. In some embodiments about $1 \times 10^5$ cells may be administered to the subject. In some embodiments about $1 \times 10^6$ cells may be administered to the subject. In other embodiments about $1 \times 10^7$ cells may be administered to the subject. In some embodiments about $1 \times 10^8$ cells may be administered to the subject.

Preferred features of the second and subsequent aspects of the invention are as described for the first aspect mutatis mutandis The examples that follow are illustrations not meant to limit the claimed invention

EXAMPLES

Materials and Methods
FLOW Cytometery Methods:

Cell monolayers were lifted from their substrate and disaggregated using trypsin (Gibco). Trypsin was removed and the cells washed in PBS and finally resuspended in PBS with 1% FBS (Gibco). Samples were separated equally into 5 tubes containing the following antibodies at a dilution of 1:50.

TABLE 3

| Tube | Antibodies |
| --- | --- |
| Tube 1 | Negative control |
| Tube 2 | FITC Anti-human SSEA-1 |
| | Alexa Fluor ® 647 Anti-human SSEA-3 |
| | Antibody PE Anti-human TRA-1-81 |
| Tube 3 | Alexa Fluor ® 488 Anti-human SSEA-4 |
| | Alexa Fluor ® 647 Anti-human TRA-1-60-R |
| Tube 4 | FITC Mouse IgM, λ Isotype Ctrl Antibody |
| | APC Rat IgM, κ Isotype Ctrl Antibody |
| | PE Mouse IgM, κ Isotype Ctrl Antibody |
| Tube 5 | Alexa Fluor ® 647 Mouse IgM, κ Isotype Ctrl |
| | Antibody Alexa Fluor ® 488Mouse IgG3 Isotype |
| | Ctrl Antibody |

Cells were incubated for 30 minutes at 4° C. after which time the cells were washed in PBS. Cells were then run on a Becton Dickinson FACSCalibur™ flow cytometer using BD FACSFlow™ sheath fluid.

Immunocytochemistry Methods:
Visualization of Tra-1-60 Expression

Cell monolayers were fixed with 4% PFA for 10 minutes and then washed with PBS (Gibco). A blocking solution containing 10% normal goat serum and 1% BSA (Sigma) was applied for 1 hour at room temperature. Tra-1-60 mouse antibody (Abcam ab16288) was applied at a dilution of 1:100 in 1% BSA and 1% normal goat serum in PBS overnight at 4° C. After removal of the antibody the cells were washed with PBS and incubated with anti mouse secondary antibody (goat anti mouse Alexa Fluor® 488 (Molecular Probes)) at 1:200 in 0.1% BSA, 1% goat serum in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Nanog Expression Cell monolayers were fixed with 4% PFA for 10 minutes and then washed with PBS (Gibco). Cells were permeabilised with 0.4% triton X-100 for 15 minutes at room temperature. A blocking solution containing 10% normal goat serum (Sigma) was applied for 1 hour at room temperature. Nanog rabbit antibody (Abcam ab21624) was applied at a dilution of 1:100 in 2.5% BSA and 10% normal goat serum in PBST overnight at 4° C. After removal of the antibody the cells were washed with PBS and incubated with anti rabbit secondary antibody (goat anti rabbit Alexa Fluor® 488 (Molecular Probes)) at 1:200 in 1% BSA, 1% goat serum in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Oct4 Expression Cell monolayers were fixed with 4% PFA for 10 minutes and then washed with PBS (Gibco). Cells were incubated with 100% ethanol for 2 minutes at room temperature. A blocking solution containing 10% normal goat serum and 1% BSA (Sigma) and 0.1% triton X-100 was applied for 1 hour at room temperature. Oct4 mouse antibody (Santa Cruz SC-5279) was applied at a dilution of 1:50 in 1% blocking buffer overnight at 4° C. After removal of the antibody the cells were washed with PBS and incubated with anti mouse secondary antibody (goat anti mouse Alexa Fluor® 488 (Molecular Probes)) at 1:400 in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Collagen Type I Expression Cell monolayers were fixed with 4% PFA for 10 minutes and then washed with PBS (Gibco). Dako cytomation protein block was applied for 1 hour at room temperature. Collagen type I mouse antibody (Sigma) was applied at a dilution of 1:200 in Dako REAL antibody diluent overnight at 4° C. After removal of the antibody the cells were washed with PBS and incubated with anti mouse secondary antibody (goat anti mouse Alexa Fluor® 488 (Molecular Probes)) at 1:1000 in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Collagen Type II Expression Cell monolayers were fixed with 4% PFA for 10 minutes and then washed with PBS (Gibco). Dako cytomation protein block was applied for 1 hour at room temperature. Collagen type II mouse antibody (CII-C1 clone, University of Iowa hybridoma bank) was applied at a dilution of 1:20 in Dako REAL antibody diluent overnight at 4° C. After removal of the antibody the cells were washed with PBS and incubated with anti mouse secondary antibody (goat anti mouse Alexa Fluor® 488 (Molecular Probes)) at 1:1000 in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Collagen Type X Expression Cell monolayers were fixed with 4% PFA for 10 minutes and then washed with PBS (Gibco). Dako cytomation protein block was applied for 1 hour at room temperature. Collagen type X mouse antibody (Sigma) was applied at a dilution of 1:20 in Dako REAL antibody diluent overnight at 4° C. After removal of the antibody the cells were washed with PBS and incubated with anti mouse secondary antibody (goat anti mouse Alexa Fluor® 488 (Molecular Probes)) at 1:1000 in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Cbfa1/RunX2 Expression Cell monolayers were fixed with 4% PFA for 10 minutes and then washed with PBST. A blocking solution containing 10% normal goat serum and 1% BSA (Sigma) and 0.1% triton X-100 was applied for 1 hour at room temperature. Cbfa1 rat antibody (R&D MAB2006) was applied at a dilution of 1:200 in 1% blocking buffer overnight at 4° C.

After removal of the antibody the cells were washed with PBST and incubated with anti rat secondary antibody (goat anti rat Alexa Fluor® 488 (Molecular Probes)) at 1:400 in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Visualization of Ki67 Expression Cell monolayers were fixed with 4% PFA for 10 minutes and then washed with PBS (Gibco). Cells were permeabilised with 0.25% triton X-100 for 10 minutes at room temperature. A blocking solution containing 10% normal goat serum (Sigma) and 1% BSA in PBST was applied for 1 hour at room temperature. Ki67 rabbit antibody (Abcam ab15580) was applied at a dilution of 1:100 in 1% BSA in PBST overnight at 4° C. After removal of the antibody the cells were washed with PBS and incubated with anti rabbit secondary antibody (goat anti rabbit Alexa Fluor® 488 (Molecular Probes)) at 1:200 in 1% BSA, 10% goat serum in PBS at room temperature for 1 hour. After further PBS washes with cells were stained with DAPI (Molecular Probes) at 1:1000 in PBS for 10 minutes. Cells were then mounted in fluorescent mountant (Dako) with a coverslip and visualised using a Zeiss fluorescent microscope Von Kossa Assay Cell monolayers were fixed with 4% PFA for 10 minutes and then washed with PBS (Gibco). After further washing with ddH$_2$O the samples were incubated with 5% silver nitrate in ddH$_2$O under strong light for 1 hour. After further washes with ddH$_2$O the samples were incubated with 5% sodium thiosulphate for 5 minutes. After further washes in ddH$_2$O the samples could be imaged on a brightfield microscope.

Visualisation of LDH Activity

Sections of tissue were made 10 μm thick on a cryostat and maintained at −20° C. until use. Polypep™ stock solution: 4% Polypep™, 0.05M gly-gly, 0.017M NaOH in ddH$_2$O. Reaction mixture: (60 mM Lactic acid, 1.75 mg/ml Nicotinamide Adenine Nucleotide, 3 mg/ml Nitroblue Tetrazolium in Polypep™ stock (all chemicals from Sigma)). Add reaction mixture to the samples and incubate at 37° C. for 3 hours. Samples are then rinsed in ddH$_2$O, then acetone and finally in PBS before mounting and imaging on a brightfield microscope.

Culture Media

Chondrogenic media: DMEM (Sigma D5671), 1% insulin, transferrin, selenium (6.25 ng/ml insulin, 6.25 mg transferrin, 6.25 ng/ml selenious acid, 1.25 mg/ml bovine, serum albumin, and 5.35 mg/ml linoleic acid) (BD Biosciences 354352), 1% L-glutamine (Gibco 25036), 1% non-essential amino acids (Gibco 11140), 1% sodium pyruvate (Sigma S8636), 350 μM L-proline (Sigma P5607), 0.1 μM Dexamethasone (Calbiochem 265005), 172.7 μM ascorbic acid (Sigma A8960), 10 ng/ml TGF-β3

Dedifferentiation media: DMEM (Sigma D5671), 10% FBS (Gibco 10500-064)

Osteogenic media: KnockOut DMEM (Gibco 10829), 10% FBS (Gibco 10500-064), 1% L-glutamine (Gibco 25036), 1% non-essential amino acids (Gibco 11140), Beta mercaptoethanol (Gibco 31350-010), 0.1 μM Dexamethasone (Calbiochem 265005), 50 μM ascorbic acid (Sigma A8960), 10 mM Beta glycerophosphate (Calbiochem 35675)

Example 1

Production of Chondrocyte Progenitor Cells

The DCCPCs were produced using a protocol as follows. Initially H7 ES cells were grown to 80% confluency using Matrigel® coated flasks and standard ES culture conditions. At this point the media was replaced with chondrogenic media. The cells remained in their original flasks and still on Matrigel® thus reducing cost and handling. Cells were cultured in these conditions for a further 14 days with chondrogenic media replaced 3 times a week. On day 14 the cell layer was washed with PBS and the chondrogenic media replaced with dedifferentiation medium. Again the cells remained in their original flasks. After a further 5 days in culture the cells showed signs of dedifferentiation and were trypsin passaged as single cells.

Materials

The materials used were: conditioned media, bFGF (Peprotech), tissue culture flasks (Nunc), Matrigel® (BD Biosciences), DMEM (Sigma), and FBS (Gibco).

Protocol hESCs were cultured to confluency on Matrigel® in either T25 or T75 flasks under standard feeder free hESC culture conditions with conditioned media supplemented with 10 ng/ml bFGF. Then the media was aspirated and the cells washed with PBS. Subsequently, full chondrogenic media was applied to the cells (DMEM (Gibco), $10^{-7}$ M Dexamethasone (Calbiochem), ITS+Premix (6.25 ng/ml insulin, 6.25 mg transferrin, 6.25 ng/ml selenious acid, 1.25 mg/ml bovine serum albumin, and 5.35 mg/ml linoleic acid, BD Biosciences), 40 μg/ml L-proline (Sigma), 50 μg/ml ascorbic acid (Sigma), 100 μg/ml sodium pyruvate (Sigma) and 10 ng/ml TGF-β3 (Peprotech)) Volumes used were comparable to those used in routine culture i.e. 7 ml for T25 and 15 ml for T75.

The cells were then cultured in the chondrogenic media for 14 days with media changes 3 times a week. On day 14 the cells appeared condensed into colonies surrounded by clumps of dead and floating cells. The media was aspirated and the cells were washed with PBS.

The media was then replaced with DMEM with 10% FBS (Gibco) ("dedifferentiation media") and cultured for a further 5 days with media changes 3 times a week. During these 5 days the cells proliferated and migrated out of the colonies such that the flask was >80% confluent by day 5. At this stage the cells are DCCPC of the invention.

On day 5 the cells were passaged with trypsin using the standard method. The vast majority of cells lifted as single cells within 5 minutes. Larger clumps of colonies were lifted from the surface by tapping the flask or pipetting the media. DMEM with FBS was added to stop the trypsin. Cells were spun out of suspension and the trypsin supernatant removed. Cells were passed through a 50 μm pore sized filter in order to obtain a single cell suspension in dedifferentiation media.

Cells were then plated onto plastic or Matrigel®. Alternatively cells were made into constructs using the standard method used for the hESCs (250,000 cells in 1 ml chondrogenic media in a 15 ml tube spun at 800 rpm for 5 minutes and cultured in this format for 7-21 days with media changes and centrifugation every 3 days. Where the construct method was used, the cells formed a construct within 16-48 hours in chondrogenic media. Where the plating method was used, cells were given 24 hours in dedifferentiation media to adhere to the surface before changing to chondrogenic media.

It was found that using these conditions DCCPCs plated onto plastic will maintain cell number but will not proliferate to any degree in the dedifferentiation media, i.e. they will not bulk up under these conditions. It was also found that plastic adherent cells expressed no ES or MSC markers. When Matrigel® was used as a substrate a higher plating efficiency was observed. DCCPCs on the Matrigel® surface showed evidence of proliferation when the cells were maintained in de-differentiation media. When DCCPCs were plated onto a Matrigel® substrate and maintained in EB media (Knockout™ D-MEM (Gibco), 10% FBS (Gibco), 1% L-glutamine (Gibco) 1% non-essential amino acids (Gibco) and 0.1 mM Beta mercaptoethanol (Gibco)) the cells showed a high rate of proliferation with no loss of chondrogenic potential.

Example 2

Morphology

The morphology of the cells changes dramatically throughout the protocol. After 14 days in our chondrogenic medium the cells show classic chondrocyte morphology with rounding up of the cell body and clustering of cells into dense colonies (FIG. 1). On day 14 the media is changed to dedifferentiation media and at days 15 through 19 in dedifferentiation media, the cells show a fibroblast like morphology and start to repopulate the culture surface A high proportion of the original ES cells died and formed rafts of dead cells that appeared as phase bright clumps just above the cell layer. These clumps could be washed off but not without substantial agitation. After 14 days the confluency was as low as 20%. However, the increase in colony density suggested that this decrease in confluency is not directly related to a decrease in cell number.

After replacement of the chondrogenic medium with de-differentiation media, cell morphology changed dramatically. Cells migrated out of the colonies (as seen using time-lapse photomicrography) and took on a more fibroblast-like morphology. Cells proliferated and over the next 5 days started to repopulate the flask. The rafts of dead cells also washed off during this dedifferentiation stage such that by day 19 there were no dead cells left. At this point the cells are still in their original flasks and thus on the original Matrigel® coating. In this state the cells proliferate. It is only after the trypsin treatment and plating onto plastic that the DCCPC stop proliferating.

The DCCPC cells had a morphology different to that of isolated primary chondrocytes. The DCCPC grew as single motile cells, and moved away from dense cell clusters. This was very unlike the more rounded primary chondrocytes that actively form condensed 3 dimensional colonies.

Example 3

Characterisation of the DCCPCs

The de-differentiated cells were trypsin passaged and detached from the Matrigel® (and also plastic in later time points) in <5 minutes, as single cells. At this point the suspension of cells was used either for construct formation or the plastic adherent cells seeded for characterisation.
Plastic Adherent Cells:

Plastic adherent DCCPCs maintained in de-differentiation media analysed using FLOW cytometry showed no ES pluripotency markers or MSC markers.

In agreement with the FLOW data, immunocytochemistry using a different Tra-1-60 antibody showed no evidence of TRA-1-60 protein expression in the DCCPCs. Tra-1-60 staining was not present on the plastic adherent DCCPCs. Undifferentiated H7 ES cells were used as a control for the antibody and showed bright membrane associated staining. After counting 1053 cells no TRA-1-60 positive cells were seen in the DCCPC population. Therefore TRA-1-60 protein expression is undetectable in this population.

The DCCPCs did not express the pluripotency marker Oct4 as determined by ICC. No evidence of Oct4 nuclear staining was seen in the DCCPCs. H7 ES cells used as positive controls for the antibody show bright nuclear staining. Cells incubated in the absence of primary antibody were used as a negative control for the staining. Out of 1537 cells counted, none showed nuclear Oct4 staining.

The DCCPCs did not express the pluripotency marker Nanog as determined by ICC. H7 ES cells used as positive controls for the antibody show bright nuclear staining. Cells incubated in the absence of primary antibody were used as a negative control for the staining. Out of 479 cells counted, none showed nuclear Nanog staining suggesting that Nanog protein expression was undetectable in this population.

The plastic adherent DCCPCs were also analysed by ICC for collagen II expression, a marker of chondrogenesis, and CBFA1/RunX2 a nuclear marker for osteogenesis and hypertrophic chondrocytes—although it is not limited to these cell types. The majority of DCCPCs are positive for CBFA1/RunX2 (FIG. 2), unlike primary (non-hypertrophic) chondrocytes that lack CBFA1/RunX2 protein expression. 99 out of 1482 counted cells (~7%) showed no collagen II expression. The rest of the cells showed a low level of intracellular collagen II protein expression.

In FIG. 2, the nuclear cbfa1/RunX2 stain was found to be present in 1336 out of 1575 cells. Therefore 85% of plastic adherent DCCPC show nuclear CBFA1/RunX2 protein expression.
DCCPCs in Construct Format As mentioned previously the DCCPCs can be cultured as a construct in order to redifferentiate the cells into chondrocytes. 250,000 cells in 1 ml chondrogenic media were placed in a 15 ml tube and spun at 800 rpm for 5 minutes and cultured in this format for 7-21 days with media changes and centrifugation every 3 days. Where this method was used, the cells formed a three dimensional construct within 16-48 hours in chondrogenic media. As with the plastic adherent cells, the cells within the construct format were also analyzed. The analyzed cells had been in construct format for 7, 14 and 21 days.

The growth state of the DCCPC-generated construct was investigated with antibodies raised against Ki67. Antibodies raised against this antigen will pick up cells in all stages of the cell cycle and only those in G0 will not stain. There was no evidence of nuclear Ki67 staining in any of the DCCPCs constructs suggesting that the cells are no longer cycling (quiescent), are not proliferative.

Pluripotency markers were investigated within the construct format by ICC. No Oct4, TRA-1-60 or Nanog protein expression was found in any of the cell constructs be this at day 7, 14 or 21. Pelleted ES cells were used as a positive control for these assays.

Example 4

Chondrogenic Re-Differentiation of Plastic Adherent DCCPCs

Chondrogenic Re-Differentiation:

DCCPCs were re-differentiated for a further 21 days on plastic by application of chondrogenic media. Collagen protein expression was investigated to determine whether the cells were becoming chondrocyte like. As previously mentioned the DCCPCs show low collagen type II protein expression when analysed by ICC. However, when the plastic adherent DCCPCs are treated with chondrogenic media the collagen type II protein expression is increased. In contrast collagen type X expression is not present throughout the DCCPC protocol and does not increase after re-differentiation. Together this data suggests that after treatment with chondrogenic media the DCCPC are differentiating towards the chondrocyte lineage but are not becoming hypertrophic.

Osteopenic Re-Differentiation:

DCCPCs were analysed to see if they would differentiate into osteoblasts when cultured in osteogenic medium. Although not osteoblast specific collagen type I is essential for bone formation. After 21 days of culture in osteogenic medium the cells produced extracellular collagen type I detected in ICC assays (FIG. 3). The formation of collagen type I is known to be upregulated by primary chondrocytes that dedifferentiate when cultured in a monolayer format on plastic, hence the appearance of the protein here is not a conclusive marker of osteogenesis. The differentiated DCCPCs were unable to mineralise the excreted matrix when analysed using a von kossa reaction. The von Kossa reaction is accepted to be a marker of calcium ions found in mineralised tissue. Mineralisation is a requirement of bone formation and its absence here indicates that the cells are not functional osteoblasts. As a control H1 hESC directly treated with this same osteogenic medium were shown to produce mineralised matrix. Thus this data suggests that the DCCPCs protocol has restricted differentiation potential, indicative of a degree of lineage commitment. The protocol would seem to be limiting the differentiation potential of the cells to the chondrogenic lineage.

Example 5

Chondrogenic Re-Differentiation of DCCPCs in Construct Format

DCCPCs that were made into the construct format were analysed for cell viability using the lactate dehydrogenase (LDH) assay. In this assay all the cells showed a dark stain indicative of active LDH. This data suggests that the whole three dimensional construct is viable at days 7, 14 and 21.

Primary human articular cartilage tissue is composed of a large amount of extracellular matrix such that less than 2% by volume of the mature tissue is occupied by chondrocytes (Hunziker, Quinn et al. 2002). The composition of the matrix produced by the chondrocytes is important for its function, and can also be used as a marker of chondrogenic differentiation.

Alcian blue staining at pH 1 was used to visualise glycosamino-glycans (GAGs) other than hyaluronic acid. DCCPCs constructs showed relatively low staining except at day 14. Safranin O staining was also used to analyse the GAG content of the matrix produced by the DCCPC. Safranin O staining (which uniformly stains GAGs) was lowest in the day 7 samples and increased slightly by day 14. There was then a very dramatic increase at day 21. Together this data suggest that GAG content of the DCCPCs constructs increases throughout culture and that it is predominantly an increase in hyaluronic acid and other acidic GAGs.

Collagens contribute approx 60% of the dry weight of articular cartilage. Collagen type II accounts for 90-95% of this collagen component. DCCPC constructs show low levels of collagen type II staining at day 7. The level of staining increases throughout the construct through days 14 and 21 that correlates with the increase seen in GAG content of the matrix. Day 7 DCCPC constructs were also analysed for collagens type I and type X. No collagens were observed at this early time point.

Constructs generated from the DCCPCs rapidly grow in size from day 14 to day 21. This size increase appears to be due to matrix production rather than cell proliferation since the Ki67 assay shows no cells in the cell cycle. DAPI staining shows very few cells per construct volume in the day 21 section.

Example 6

Implantation of Chondrocyte Cell Constructs in an In Vivo Model

Adult three months old male Sprague-dawley rats (immunocompetent wild type; WT) (Harlan UK limited) were used in this study. All animals were maintained under the guidelines set by the institutional Animal Care and Ethical Committee at the University of Edinburgh, and the procedures approved under a UK Home Office license. All operations were performed under general anaesthesia (2-3.5% isofluorane). Post-operative analgesia was induced by buprenorphine injections (0.05% mg/Kg) twice 24 hours post-surgery. A standard medial parapatellar approach was used to expose the knee. A 1 mm diameter chondral defect was created in the articular cartilage in the weight-bearing area of the femoral trochlea of the rat knee. One 14 day old DCCPC construct was implanted into the defect and sealed with fibrin glue (Tisseel®, Baxter Healthcare Ltd, Newbury, UK). A layered closure was performed. No immunomodulatory drugs were used. Animals were allowed to move freely postoperative with adequate analgesia. Samples were harvested after 3 weeks. Animals were sacrificed by inhalation of $CO_2$ (approved by the schedule 1 of the Animals (Scientific Procedures) Act 1986) and the dissected knees were briefly immersed in 5% polyvinyl alcohol (PVA; Sigma-Aldrich) and immediately snap-frozen in hexane (Sigma-Aldrich) maintained at −80° C.

For histological examination, frozen knees were cryosectioned (10 μm) sagittally perpendicular to the defect and mounted on histology ultra-thin tape to maintain morphology of the tissue. Cryosections were fixed in 4% (w/v) paraformaldehyde and washed in PBS. Haematoxylin & Eosin staining was used for histological analysis. For results see FIG. 4.

The skilled reader will appreciate that the invention can be modified as a matter of routine optimization, without departing from the spirit of the invention, or the scope of the appended claims

The invention claimed is:

1. A population of de-differentiated committed chondrocyte precursor cells, wherein the de-differentiated committed chondrocyte precursor cells are the in vitro progeny of human embryonic stem (hES) cells and characterized by 85% or more of the cells expressing CBFA1 and by the loss of transdifferentiation potential to form osteoblasts when cultured in osteogenic medium.

2. The population of claim 1, wherein 1% or less of the cells express Oct4, Nanog and/or TRA-1-60.

3. The population of claim 1, wherein 1% or less of the cells express Ki67.

4. The population of claim 1, further comprising human embryonic stem (hES) cells, wherein the de-differentiated committed chondrocyte precursor cells are the in vitro progeny of the hES cells.

5. A first and a second population of cells, comprising: a) a first in vitro population of cells comprising human embryonic stem (hES) cells; and b) a second in vitro population of cells comprising de-differentiated committed chondrocyte precursor (DDPC) cells that are the progeny of the hES cells, wherein 85% or more of the DDPCs express CBFA1 and wherein the DDPCs are characterized by the loss of trans-differentiation potential to form osteoblasts when cultured in osteogenic medium.

* * * * *